United States Patent
O'Connor et al.

(10) Patent No.: US 9,879,061 B2
(45) Date of Patent: Jan. 30, 2018

(54) INHIBITION OF AXL/GAS6 SIGNALING IN THE TREATMENT OF LIVER FIBROSIS

(71) Applicants: The Board of Trustees of the Leland Stanford Junior University, Stanford, CA (US); Aravive Biologics, Inc., Houston, TX (US)

(72) Inventors: Patrick O'Connor, Palo Alto, CA (US); Raymond Tabibiazar, Menlo Park, CA (US); Amato J. Giaccia, Stanford, CA (US); Erinn Bruno Rankin, Waltham, MA (US); Jennifer R. Cochran, Stanford, CA (US); Douglas Jones, Cambridge, MA (US); Mihalis Kariolis, Stanford, CA (US); Katherine Fuh, Palo Alto, CA (US); Yu Miao, Sunnyvale, CA (US)

(73) Assignees: The Board of Trustees of the Leland Stanford Junior University, Stanford, CA (US); Aravive Biologics, Inc., Houston, TX (US)

(*) Notice: Subject to any disclaimer, the term of this patent is extended or adjusted under 35 U.S.C. 154(b) by 1026 days.

(21) Appl. No.: 13/714,875

(22) Filed: Dec. 14, 2012

(65) Prior Publication Data

US 2013/0189254 A1    Jul. 25, 2013

Related U.S. Application Data

(60) Provisional application No. 61/576,304, filed on Dec. 15, 2011.

(51) Int. Cl.
| | | |
|---|---|---|
| *C07K 14/47* | (2006.01) |
| *C07K 16/28* | (2006.01) |
| *C07K 16/40* | (2006.01) |
| *C07K 16/18* | (2006.01) |
| *C07K 19/00* | (2006.01) |
| *G01N 33/50* | (2006.01) |
| *G01N 33/68* | (2006.01) |
| *A61K 45/06* | (2006.01) |
| *A61K 38/10* | (2006.01) |
| *C07K 16/22* | (2006.01) |
| *C07K 14/705* | (2006.01) |
| *A61K 39/00* | (2006.01) |

(52) U.S. Cl.
CPC .......... *C07K 14/4703* (2013.01); *A61K 38/10* (2013.01); *A61K 45/06* (2013.01); *C07K 14/705* (2013.01); *C07K 16/18* (2013.01); *C07K 16/22* (2013.01); *C07K 16/28* (2013.01); *C07K 16/2863* (2013.01); *C07K 16/40* (2013.01); *C07K 19/00* (2013.01); *G01N 33/5023* (2013.01); *G01N 33/689* (2013.01); *G01N 33/6893* (2013.01); *A61K 2039/505* (2013.01); *C07K 2317/34* (2013.01); *C07K 2319/30* (2013.01); *G01N 2500/10* (2013.01); *G01N 2800/24* (2013.01); *G01N 2800/245* (2013.01); *G01N 2800/347* (2013.01); *G01N 2800/364* (2013.01); *G01N 2800/50* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | |
|---|---|---|
| 5,468,634 A | 11/1995 | Liu |
| 5,538,861 A | 7/1996 | Schneider et al. |
| 6,096,527 A | 8/2000 | Godowski et al. |
| 6,737,056 B1 | 5/2004 | Presta |
| 7,709,482 B2 | 5/2010 | Goff et al. |
| 8,168,415 B2 | 5/2012 | Graham et al. |
| 8,618,254 B2 | 12/2013 | Giaccia et al. |
| 9,074,192 B2 | 7/2015 | Giaccia et al. |
| 9,266,947 B2 | 2/2016 | Giaccia et al. |
| 2005/0186571 A1 | 8/2005 | Ulrich et al. |
| 2007/0128200 A1 | 6/2007 | Yang et al. |
| 2009/0042826 A1 | 2/2009 | Mor et al. |
| 2009/0087431 A1 | 4/2009 | Yaworsky et al. |
| 2010/0266604 A1 | 10/2010 | Rothlin et al. |
| 2011/0014173 A1 | 1/2011 | Graham et al. |

(Continued)

FOREIGN PATENT DOCUMENTS

| | | |
|---|---|---|
| EP | 1897940 | 3/2008 |
| JP | 2005278631 | 10/2005 |

(Continued)

OTHER PUBLICATIONS

The Merck Manuals Online Medical Library, [online]. Whitehouse Station, NJ: Merck Research Laboratories, 2006-2007. [retrieved on Feb. 6, 2016]. Retrieved from the Internet: < http://www.merckmanuals.com/professional/hepatic-and-biliary-disorders/fibrosis-and-cirrhosis/hepatic-fibrosis >. Hepatic Fibrosis. pp. 1-6.*
Barcena et al. (J Hepatol 2015, 63:670-8).*
Brand et al., "Prospect for Anti-HER2 Receptor Therapy in Breast Cancer", Anticancer Res. (2006); 26:463-70.
Sawabu et al. "Growth Arrest-Specific Gene 6 and Axl Signaling Enhances Gastric Cancer Cell Survival via Akt Pathway" Mol. Carcinog. (2007); vol. 46, No. 2, pp. 155-164.
Talmadge et al., "AACR Centennial Series: The Biology of Cancer Metastasis: Historical Perspective", Cancer Res; (2010); 70 (14); 5649-69.

(Continued)

*Primary Examiner* — Sharon X Wen
(74) *Attorney, Agent, or Firm* — Pamela J. Sherwood; Bozicevic, Field & Francis LLP

(57) ABSTRACT

Compositions and methods are provided for alleviating endometriosis, kidney disease, inflammatory disease and/or transplant rejection in a mammal by administering a therapeutic dose of a pharmaceutical composition that inhibits AXL, MER or Tyro3 protein activity, for example by competitive or non-competitive inhibition of the binding interaction between AXL, MER or Tyro3 and its ligand GAS6.

4 Claims, No Drawings

(56) References Cited

U.S. PATENT DOCUMENTS

| | | | |
|---|---|---|---|
| 2011/0237498 | A1 | 9/2011 | Raymond et al. |
| 2013/0189254 | A1 | 7/2013 | O'Conner et al. |
| 2015/0315552 | A1 | 11/2015 | Giaccia et al. |
| 2015/0315553 | A1 | 11/2015 | Giaccia et al. |
| 2016/0108378 | A1 | 4/2016 | Giaccia et al. |

FOREIGN PATENT DOCUMENTS

| | | |
|---|---|---|
| JP | 2005532805 | 11/2005 |
| WO | 2004008147 | 1/2004 |
| WO | 2004/092735 | 10/2004 |
| WO | 2004/108748 | 12/2004 |
| WO | 20006058202 | 6/2006 |
| WO | 2008098139 | 8/2008 |
| WO | 2009/005813 | 1/2009 |
| WO | 2010/014755 A1 | 2/2010 |
| WO | 2010/130751 A1 | 11/2010 |
| WO | 2011/014457 | 2/2011 |
| WO | 2011091305 | 7/2011 |
| WO | 2011/159980 | 12/2011 |
| WO | 2014093690 | 6/2014 |
| WO | 2014093707 | 6/2014 |
| WO | 2006/118308 A1 | 11/2016 |

OTHER PUBLICATIONS

Weidel et al., "Genetically Engineered Fusion Proteins for Treatment of Cancer", Cancer Genomics & Proteomics (2012); 9:357-72.
Cerchia; et al., "Targeting Axl with an high-affinity inhibitory aptamer", Mol Ther (Dec. 2012), 20(12):2291-2303.
Healy; et al. "Gas 6 promotes Axl-mediated survival in pulmonary endothelfal cells", Am J Physiol Lung Cell Mol Physiol (Jun. 2001), 280(6):L1273-1281.
Mark; et al., "Characterization of Gas6, a Member of the Superfamily of G Domain-containing Proteins, as a Ligand for Rse and Axl", J Biol Chem (Apr. 1996), 271(16):9785-9789.
Nagata; et al. "Identification of the product of growth arrest-specific gene 6 as a common ligand for Axl, Sky, and Mer receptor tyrosine kinases", J Biol Chem (Nov. 1996), 271(47):30022-30027.
"Quantikine ELISA. Mouse Gas6 Immunoassay", R&D Systems, Inc. (Apr. 2013), Catalog No. MGAS60, 12 pgs., Retrieved from the Internet on Mar. 18, 2014, http://www.rndsystems.com/pdf/MGAS60.pdf.
Altomare; et al. "AKT and mTOR phosphorylation is frequently detected in ovarian cancer and can be targeted to disrupt ovarian tumor cell growth", Oncogene (Jul. 2004), 23(34):5853-5857.
Angelillo-Scherrer; et al. "Deficiency or inhibition of Gas6 causes platelet dysfunction and protects mice against thrombosis", Nat Med (Feb. 2001), 7(2):215-221.
Armstrong; et al. "Intraperitoneal cisplatin and paclitaxel in ovarian cancer", N Engl J Med (Jan. 2006), 354(1):34-43.
Berclaz; et al. "Estrogen dependent expression of the receptor tyrosine kinase axl in normal and malignant human breast", Ann Oncol (Jun. 2001), 12(6):819-824.
Bonome; et al. "Expression profiling of serous low malignant potential, low-grade, and high-grade tumors of the ovary", Cancer Res (Nov. 2005), 65(22):10602-10612.
Cheng; et al. "AKT2, a putative oncogene encoding a member of a subfamily of protein-serine/threonine kinases, is amplified in human ovarian carcinomas", PNAS (Oct. 1992), 89(19):9267-9271.
Choi; et al. "Gonadotropins activate proteolysis and increase invasion through protein kinase A and phosphatidylinositol 3-kinase pathways in human epithelial ovarian cancer cells", Cancer Res (Apr. 2006), 66(7):3912-3920.
Egeblad; et al. "New functions for the matrix metalloproteinases in cancer progression" Nat Rev Cancer (Mar. 2002), 2(3):161-174.
Erler; et al. "Lysyl oxidase is essential for hypoxia-induced metastasis", Nature (Apr. 2006), 440(7088):1222-1226.

Fridell; et al. "GAS6 induces Axl-mediated chemotaxis of vascular smooth muscle cells", J Biol Chem (Mar. 1998), 273(12):7123-7126.
Goruppi; et al. "Gas6-mediated survival in NIH3T3 cells activates stress signalling cascade and is independent of Ras", Oncogene (Jul. 1999), 18(29):4224-4236.
Guo; et al. "Increased staining for phosphorylated AKT and nuclear factor-kappaB p65 and their relationship with prognosis in epithelial ovarian cancer", Pathol Int (Dec. 2008), 58(12):749-756.
Holland; et al. "Multiple roles for the receptor tyrosine kinase axl in tumor formation", Cancer Res (Oct. 2005), 65(20):9294-9303.
Hua; et al."Estrogen and progestin regulate metastasis through the PI3K/AKT pathway in human ovarian cancer", Int J Oncol (Nov. 2008), 33(5):959-967.
Hutterer; et al."Axl and growtharrest-specific gene 6 are frequently overexpressed in human gliomas and predict poor prognosis in patients with glioblastoma multiforme", Clin Cancer Res (Jan. 2008), 14(1):130-138.
Janssen; et al. "A novel putative tyrosine kinase receptor with oncogenic potential", Oncogene (Nov. 1991), 6(11):2113-2120.
Kenny; et al. "The initial steps of ovarian cancer cell metastasis are mediated by MMP-2 cleavage of vitronectin and fibronecti", J Clin Invest (Apr. 2008), 118(4):1367-1379.
Koorstra; et al. "The Axl receptor tyrosine kinase confers an adverse prognostic influence in pancreatic cancer and represents a new therapeutic target", Cancer Biol Ther (Apr. 2009), 8(7):618-626.
Kuhnert; et al. "Soluble receptor-mediated selective inhibition of VEGFR and PDGFRbeta signaling during physiologic and tumor angiogenesis", PNAS (Jul. 2008), 105(29):10185-10190.
Kuo; et al. "Comparative evaluation of the antitumor activity of antiangiogenic proteins delivered by gene transfer", PNAS (Apr. 2001), 98(8):4605-4610.
Lancaster; et al. "Identification of genes associated with ovarian cancer metastasis using microarray expression analysis", Int J Gynecol Cancer (Sep.-Oct. 2006), 16(5)1733-1745.
Lengyel; et al. "Expression of latent matrix metalloproteinase 9 (MMP-9) predicts survival in advanced ovarian cancer", Gynecol Oncol (Aug. 2001), 82(2):291-298.
Li; et al. "Axl as a potential therapeutic target in cancer: role of Axl in tumor growth, metastasis and angiogenesis", Oncogene (Oct. 2009), 28(39):3442-3455.
Linger; et al. "TAM receptor tyrosine kinases: biologic functions, signaling, and potential therapeutic targeting in human cancer", Adv Cancer Res (2008), 100:35-83.
Liu; et al. "AKT2, a member of the protein kinase B family, is activated by growth factors, v-Ha-ras, and v-src through phosphatidylinositol 3-kinase in human ovarian epithelial cancer cells", Cancer Res, (Jul. 1998), 58(14):2973-2977.
Lu; et al. "Homeostatic regulation of the immune system by receptor tyrosine kinases of the Tyro 3 family", Science (Jul. 2001), 293(5528):306-311.
Martin; et al. "Management of recurrent ovarian carcinoma: current status and future directions", Semin Oncol (Apr. 2009), 36(2):112-125.
McCloskey; et al. "GAS6 mediates adhesion of cells expressing the receptor tyrosine kinase Axl", J Biol Chem (Sep. 1997), 272(37):23285-23291.
Mills; et al. "The role of genetic abnormalities of PTEN and the phosphatidylinositol 3-kinase pathway in breast and ovarian tumorigenesis, prognosis, and therapy", Semin Oncol (Oct. 2001), 28(5 Suppl 16):125-141.
Nakayama; et al. "Amplicon profiles in ovarian serous carcinomas", Int J Cancer (Jun. 2007), 120(12):2613-2617.
Naora; et al. "Ovarian cancer metastasis: integrating insights from disparate model organisms", Nat Rev Cancer (May 2005), 5(5):355-366.
Nielsen-Preiss; et al. "Adhesion-related kinase induction of migration requires phosphatidylinositol-3-kinase and ras stimulation of rac activity in immortalized gonadotropin-releasing hormone neuronal cells", Endocrinology (Jun. 2007), 148(6):2806-2814.
O'Bryan; et al."axl, a transforming gene isolated from primary human myeloid leukemia cells, encodes a novel receptor tyrosine kinase", Mol Cell Biol (Oct. 1991), 11(10):5016-5031.

(56) References Cited

OTHER PUBLICATIONS

O'Bryan; et al. "The transforming receptor tyrosine kinase, Axl, is post-translationally regulated by proteolytic cleavage", J Biol Chem (Jan. 1995), 270(2):551-557.

Patel: et al., "Engineering an APRIL-specific B Cell Maturation Antigen", The Journal of Biological Chemistry (Apr. 2004), 279(16):16727-16735.

Perigny; et al. "Role of immunohistochemical overexpression of matrix metalloproteinases MMP-2 and MMP-11 in the prognosis of death by ovarian cancer", Am J Clin Pathol (Feb. 2008), 129(2):226-231.

Rankin; et al. "Renal cyst development in mice with conditional inactivation of the von Hippel-Lindau tumor suppressor", Cancer Res (Mar. 2006), 66(5):2576-2583.

Sahai; et al. "Illuminating the metastatic process", Nat Rev Cancer (Oct. 2007), 7(10):737-749.

Sasaki; et al. "Structural basis for Gas6-Axl signalling", EMBO J (Jan. 2006), 25(1):80-87.

Satpathy; et al. "Tissue transglutaminase regulates matrix metalloproteinase-2 in ovarian cancer by modulating cAMP-response element-binding protein activity", J Biol Chem (Jun. 2009), 284(23):15390-15399.

Shieh; et al. "Expression of Axl in Lung Adenocarcinoma and Correlation with Tumor Progression", Neoplasia (Dec. 2005), 7(12):1058-1064.

Sun; et al. "Coexpression of Gas6/Axl in human ovarian cancers", Oncology (2004), 66(6):450-457.

Sutphin; et al. "Targeting the loss of the von Hippel-Lindau tumor suppressor gene in renal cell carcinoma cells", Cancer Res (Jun. 2007), 67(12):5896-5905.

Tai; et al. "Axl promotes cell invasion by inducing MMP-9 activity through activation of NF-kappaB and Brg-1", Oncogene (Jul. 2008), 27(29):4044-4055.

Tan; et al. "Mechanisms of transcoelomic metastasis in ovarian cancer", Lancet Oncol (Nov. 2006), 7(11):925-934.

Vajkoczy; et al. "Dominant-negative inhibition of the Axl receptor tyrosine kinase suppresses brain tumor cell growth and invasion and prolongs survival", Proc Natl Acad Sci U S A (Apr. 2006), 103(15):5799-5804.

Yoneda; et al. "Expression of angiogenesis-related genes and progression of human ovarian carcinomas in nude mice", J Natl Cancer Inst (Mar. 2009), 90(6):447-454.

Zhang; et al. "AXL is a potential target for therapeutic intervention in breast cancer progression", Cancer Res (Mar. 2008), 68(6):1905-1915.

Balmana et al., "BRCA in breast cancer: ESMO Clinical Recommendations", Ann Oncol., May 2009; pp. iv19-iv20, vol. 20, Supp. 4, Oxford University Press, Oxford, United Kingdom.

\* cited by examiner

INHIBITION OF AXL/GAS6 SIGNALING IN THE TREATMENT OF LIVER FIBROSIS

CROSS-REFERENCE TO RELATED APPLICATIONS

The present application claims priority to U.S. Provisional Application No. 61/576,304, filed Dec. 15, 2011, and which is expressly incorporated by reference herein in its entirety for all purposes.

FIELD OF THE INVENTION

The present invention relates to endometriosis, kidney disease, inflammatory disease and/or transplant rejection (GVHD), e.g., treatments or diagnoses of endometriosis, kidney disease, inflammatory disease and/or transplant rejection (GVHD) via pathways related to AXL, MER, Tyro3 and/or GAS6.

BACKGROUND OF THE INVENTION

Endometriosis is a female health disorder that occurs when cells from the lining of the womb (i.e., uterus, endometrium) migrate and invade other areas of the body in the abdominal cavity. This can lead to pain, irregular bleeding and problems such as infertility.

Kidney disease can include diabetic nephropathy and progressive glomerulonephritis.

Diabetic nephropathy (also known as Kimmelstiel-Wilson syndrome, nodular diabetic glomerulosclerosis, or intercapillary glomerulonephritis) is a type of kidney disease caused by angiopathy of capillaries in the kidney glomeruli. Diabetic nephropathy is characterized by nephrotic syndrome and diffuse glomerulosclerosis and is often associated with longstanding diabetes mellitus.

Progressive glomerulonephritis (also referred to as rapidly progressive glomerulonephritis (RPGN) or crescentic glomerulonephritis) is a syndrome of the kidney that is characterized by a rapid loss of renal function in combination with glomerular crescent (crescent-shaped scar) formation often seen in at least half of glomeruli. Severe injury to the kidneys' glomeruli occurs with many of the glomeruli exhibiting characteristic glomerular crescents. Without treatment the syndrome can rapidly progress into acute renal failure and even death within months.

Inflammatory disease can include liver inflammation, steatohepatitis and liver fibrosis.

Liver inflammation (such as hepatitis) is characterized by the presence of inflammatory cells in the tissue of the liver. Liver inflammation can occur due to a variety of infections or other disease indications, including viral hepatitis infections or non-viral infections. Liver inflammation can also be drug induced, and can occur in response to drugs such as alcohol, antidepressants, antihistamines, immune suppressant drugs, antihypertensives, antibiotics, antiepileptics, antidiabetics and antivirals.

Steatohepatitis (also known as fatty liver disease) is a type of liver disease that is characterized by inflammation of the liver in conjunction with fat accumulation in liver. The disease is seen in alcoholics as part of alcoholic liver disease, but also occurs in people with diabetes and obesity and can be related to metabolic syndromes. When not associated with excessive alcohol intake, the disease is referred to as non-alcoholic steatohepatitis (NASH; or non-alcoholic fatty liver disease (NAFLD)). NASH is also known as the progressive form of the relatively benign non-alcoholic fatty liver disease. Steatohepatitis of either etiology may progress to cirrhosis. NASH can also be associated with Lysosomal Acid Lipase Deficiency.

Liver fibrosis (also known as cirrhosis) is often a result of chronic liver disease and is characterized by replacement of liver tissue by fibrotic scar tissue and regenerative nodules which leads to loss of liver function. Cirrhosis can be caused by alcoholism, hepatitis B and C, and fatty liver disease, as well as other causes. Liver fibrosis is generally irreversible, and treatment usually focuses on preventing progression and managing complications. In advanced stages of liver fibrosis the only option is often a liver transplant.

Transplant rejection (graft-versus-host-disease; GVHD) is a common complication and often occurs after an allogeneic stem cell or bone marrow transplant from another person. Immune cells in the donated marrow or stem cells recognize the recipient as "foreign" and attack the recipient host's body. GVHD can also occur during a blood transfusion. Generally, the three Billingham Criteria are used for evaluating the occurrence of GVHD: an immuno-competent graft is administered that contains viable and functional immune cells; the recipient is immunologically disparate (histoincompatible); and the recipient is immuno-compromised and therefore cannot destroy or inactivate the transplanted cells.

There remains a need in the art for therapies for the treatment of endometriosis, kidney disease, inflammatory disease and/or transplant rejection (GVHD). The present invention provides for that need by providing treatment and/or diagnosis of endometriosis, kidney disease, inflammatory disease and/or transplant rejection (GVHD) disease via pathways related to AXL and/or GAS6.

BRIEF SUMMARY OF THE INVENTION

The present invention is based in part on the discovery that AXL, MER, Tyro3 and/or GAS6 related pathways are related to endometriosis, kidney disease, inflammatory disease and/or transplant rejection (GVHD). Accordingly, the present invention provides compositions and methods useful for treating endometriosis, kidney disease, inflammatory disease and/or transplant rejection (GVHD), and symptoms associated with such diseases, e.g., via inhibition of AXL, MER, Tyro3 and/or GAS6 related pathways. In addition, the present invention provides reagents and methods useful for determining the likelihood of a subject to be susceptible to endometriosis, kidney disease, inflammatory disease and/or transplant rejection (GVHD), e.g., via detecting the level of activity of AXL, MER, Tyro3 and/or GAS6.

The present invention provides a method of treating, reducing, or preventing endometriosis, kidney disease, inflammatory disease and/or transplant rejection (GVHD) in a mammalian patient. In one embodiment, the method comprises administering one or more inhibitor agents selected from the group consisting of (a) an inhibitor of AXL, MER and/or Tyro3 activity (b) an inhibitor of GAS6 activity; and (c) an inhibitor of AXL, MER or Tyro3-GAS6 interaction. The present invention also provides a method of determining the susceptibility of a subject to endometriosis, kidney disease, inflammatory disease and/or transplant rejection, said method comprising: detecting the level of AXL, MER and/or Tyro3 activity in a biological sample from a subject; and comparing the level of the AXL MER and/or Tyro3 activity in the biological sample to a predetermined level, wherein an increase over the predetermined level is indicative of a predisposition of the subject to develop endometriosis, kidney disease, inflammatory disease and/or transplant rejection (GVHD).

In some embodiments, the present invention provides methods of treating, reducing, or preventing endometriosis, kidney disease, inflammatory disease and/or transplant rejection (GVHD) disease in a mammalian patient. In one embodiment, the method comprises administering to said patient an effective dose of a soluble AXL polypeptide or an isolated anti-GAS6 antibody or fragment thereof.

The present invention also provides a method of determining the susceptibility of a subject to endometriosis, kidney disease, inflammatory disease and/or transplant rejection (GVHD). In one embodiment, the method comprises detecting the level of AXL activity and/or GAS6 activity in a biological sample from a subject; and comparing the level of the AXL and/or GAS6 activity in the biological sample to a predetermined level, wherein an increase over the predetermined level is indicative of a predisposition of the subject to develop endometriosis, kidney disease, inflammatory disease and/or transplant rejection (GVHD).

The present invention also provides a method of determining treatment efficacy of administering an inhibitor agent comprising detecting the level of AXL, MER, Tyro3 and/or GAS6 activity in a biological sample from a subject treated with said inhibitor agent, wherein a decrease in AXL, MER, Tyro3 and/or GAS6 activity is indicative of the efficacy of treatment with the inhibitor agent.

The present invention also provides a method for determining the treatment regimen of an inhibitor agent comprising detecting the level of AXL, MER, Tyro3 and/or GAS6 activity in a biological sample from a subject treated with said inhibitor agent, and determining a treatment regimen of the inhibitor agent based on an increase or decrease in the level of AXL, MER, Tyro3 and/or GAS6 activity.

In some embodiments, the AXL, MER or Tyro3 activity level is measured by the level of AXL MER or Tyro3 mRNA expression or the level of AXL, MER or Tyro3 protein expression.

In some embodiments, the GAS6 activity level is measured by the level of GAS6 mRNA expression or the level of GAS6 protein expression.

In some embodiments, the kidney disease is diabetic nephropathy or progressive glomerulonephritis.

In some embodiments, the inflammatory disease is liver inflammation, steatohepatitis or liver fibrosis.

In some embodiments, the biological sample is selected form the group consisting of a tissue sample, a blood sample, a serum sample, a cerebrospinal fluid (CSF) sample, an ascite fluid sample, and a cell culture sample.

In some embodiments, the inhibitor is a polypeptide, a polynucleotide, a small molecule, an antibody, an antibody fragment or antibody drug-conjugate.

In some embodiments, the inhibitor agent is capable of binding to GAS6 with increased affinity compared to wild-type AXL, MER or Tyro3.

In some embodiments, the inhibitor agent binds to two or more epitopes on a single GAS6.

In some embodiments, the inhibitor agent is capable of binding to the major and minor AXL, MER or Tyro3 binding sites on a single GAS6.

In some embodiments, the inhibitor agent is capable of binding the major AXL, MER or Tyro3 binding site of GAS6 and one or more additional GAS6 epitopes on a single GAS6.

In some embodiments, the inhibitor agent is capable of binding to the minor AXL, MER or Tyro3 binding site on GAS6 and one or more additional epitopes on a single GAS6.

In some embodiments, the inhibitor agent is capable of binding two or more epitopes on a single GAS6.

In some embodiments, the inhibitor agent is capable of antagonizing the major and/or minor GAS6/receptor binding interaction, and wherein the receptor is selected from AXL, MER and Tyro3.

In some embodiments, the inhibitor agent is capable of antagonizing the major GAS6/receptor binding interaction, and wherein the receptor is selected from AXL, MER and Tyro3.

In some embodiments, the inhibitor agent is capable of antagonizing the minor GAS6/receptor binding interaction, and wherein the receptor is selected from AXL, MER and Tyro3.

In some embodiments, the inhibitor agent is a polypeptide, a polypeptide-carrier fusion, a polypeptide-Fc fusion, polypeptide-conjugate, a polypeptide-drug conjugate, an antibody, a bispecific antibody, an antibody drug conjugate, an antibody fragment, an antibody-related structure, or a combination thereof.

In some embodiments, the inhibitor agent is a natural or synthetic polypeptide.

In some embodiments, the inhibitor agent is a non-antibody polypeptide.

In some embodiments, the inhibitor agent is a darpin, an avimer, an adnectin, an anticalin, an affibody, a maxibody or a combination thereof.

In some embodiments, the inhibitor agent is a polypeptide-conjugate or an antibody-conjugate.

In some embodiments, the inhibitor agent comprises a polypeptide-polymer conjugate, and wherein the polymer is a PEG, a PEG-containing polymer, a degradable polymer, a biocompatible polymer or a hydrogel.

In some embodiments, the inhibitor agent is a polypeptide, wherein the polypeptide comprises a soluble AXL variant polypeptide wherein the AXL polypeptide lacks the AXL transmembrane domain and has at least one mutation relative to wild-type that increases affinity of the AXL polypeptide binding to GAS6 compared to wild-type AXL.

In some embodiments, the inhibitor agent is a polypeptide, wherein the polypeptide comprises a soluble MER variant polypeptide wherein said MER polypeptide lacks the MER transmembrane domain and has at least one mutation relative to wild-type that increases affinity of the MER polypeptide binding to GAS6 compared to wild-type MER.

In some embodiments, the inhibitor agent is a polypeptide, wherein said polypeptide comprises a soluble Tyro3 variant polypeptide wherein said Tyro3 polypeptide lacks the Tyro3 transmembrane domain and has at least one mutation relative to wild-type that increases affinity of the Tyro3 polypeptide binding to GAS6 compared to wild-type Tyro3.

In some embodiments, the AXL, MER or Tyro3 variant polypeptide inhibits binding between a wild-type AXL, MER and/or Tyro3 polypeptide and a GAS6 protein in vivo or in vitro.

In some embodiments, the AXL, MER or Tyro3 variant polypeptide lacks a functional fibronectin (FN) domain and/or wherein said AXL, MER or Tyro3 variant polypeptide exhibits increased affinity of the polypeptide binding to GAS6 compared to wild-type AXL, MER or Tyro3.

In some embodiments, the AXL, MER or Tyro3 variant polypeptide lacks the transmembrane domain, has more than one Ig1 domain and wherein said AXL, MER or Tyro3 variant polypeptide exhibits increased affinity of the AXL, MER or Tyro3 variant polypeptide binding to GAS6 compared to wild-type AXL, MER or Tyro3.

In some embodiments, the polypeptide has two Ig1 domains.

In some embodiments, the polypeptide has three Ig1 domains.

In some embodiments, the soluble AXL, MER or Tyro3 variant polypeptide lacks the transmembrane domain, has more than one Ig2 domain and wherein said AXL, MER or Tyro3 variant polypeptide exhibits increased affinity of the AXL, MER or Tyro3 polypeptide binding to GAS6 compared to wild-type AXL, MER or Tyro3.

In some embodiments, the polypeptide has two Ig2 domains.

In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, has more than one Ig1 domain, more than one Ig2 domain, and wherein said AXL, MER or Tyro3 variant polypeptide exhibits increased affinity of the AXL, MER or Tyro3 variant polypeptide binding to GAS6 compared to wild-type AXL, MER or Tyro3.

In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, lacks a functional fibronectin (FN) domain, has more than one Ig1 domain, more than one Ig2 domain, and wherein said AXL, MER or Tyro3 variant polypeptide exhibits increased affinity of the AXL, MER or Tyro3 variant polypeptide binding to GAS6 compared to wild-type AXL, MER or Tyro3.

In some embodiments, the soluble AXL, MER or Tyro3 variant polypeptide has two Ig1 domains and two Ig2 domains.

In some embodiments, the immunoglobulin domains are connected directly.

In some embodiments, the immunoglobulin domains are connected indirectly.

In some embodiments, the polypeptide is a soluble AXL, MER or Tyro3 variant polypeptide, wherein said variant polypeptide lacks the AXL, MER or Tyro3 transmembrane domain, is capable of binding both the major and minor binding site of a single GAS6 and wherein said AXL, MER or Tyro3 variant polypeptide exhibits increased affinity of the AXL, MER or Tyro3 polypeptide binding to GAS6.

In some embodiments, the polypeptide has one Ig1 domain and lacks a functional Ig2 domain.

In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, has one Ig1 domain, lacks a functional Ig2 domain and wherein said AXL, MER or Tyro3 variant polypeptide exhibits increased affinity of the AXL, MER or Tyro3 variant polypeptide binding to GAS6 compared to wild-type AXL, MER or Tyro3.

In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, lacks a functional fibronectin (FN) domain, has one Ig1 domain, lacks a functional Ig2 domain and wherein said AXL, MER or Tyro3 variant polypeptide exhibits increased affinity of the AXL, MER or Tyro3 variant polypeptide binding to GAS6 compared to wild-type AXL, MER or Tyro3.

In some embodiments, the AXL, MER or Tyro3 variant polypeptide is a fusion protein comprising an Fc domain.

In some embodiments, the variant polypeptide lacks the AXL, MER or Tyro3 intracellular domain.

In some embodiments, the soluble AXL, MER or Tyro3 variant polypeptide further lacks a functional fibronectin (FN) domain and wherein said variant polypeptide exhibits increased affinity of the polypeptide binding to GAS6.

In some embodiments, the soluble AXL, MER or Tyro3 variant polypeptide comprises at least one amino acid modification relative to the wild-type AXL, MER or Tyro3 sequence.

In some embodiments, the soluble AXL variant polypeptide comprises at least one amino acid modification within a region selected from the group consisting of 1) between 15-50, 2) between 60-120, and 3) between 125-135 of the wild-type AXL sequence (SEQ ID NO:1).

In some embodiments, the soluble AXL variant polypeptide comprises at least one amino acid modification at position 19, 23, 26, 27, 32, 33, 38, 44, 61, 65, 72, 74, 78, 79, 86, 87, 88, 90, 92, 97, 98, 105, 109, 112, 113, 116, 118, or 127 of the wild-type AXL sequence (SEQ ID NO: 1) or a combination thereof.

In some embodiments, the soluble AXL variant polypeptide comprises at least one amino acid modification selected from the group consisting of 1) A19T, 2) T23M, 3) E26G, 4) E27G or E27K 5) G32S, 6) N33S, 7) T38I, 8) T44A, 9) H61Y, 10) D65N, 11) A72V, 12) S74N, 13) Q78E, 14) V79M, 15) Q86R, 16) D87G, 17) D88N, 18) I90M or I90V, 19) V92A, V92G or V92D, 20) I97R, 21) T98A or T98P, 22) T105M, 23) Q109R, 24) V112A, 25) F113L, 26) H116R, 27) T118A, 28) G127R or G127E, and 29) G129E and a combination thereof.

In some embodiments, the AXL variant polypeptide comprises amino acid changes relative to the wild-type AXL sequence (SEQ ID NO: 1) at the following positions: (a) glycine 32; (b) aspartic acid 87; (c) valine 92; and (d) glycine 127.

In some embodiments, the AXL variant polypeptide comprises amino acid changes relative to the wild-type AXL sequence (SEQ ID NO: 1) at the following positions: (a) aspartic acid 87 and (b) valine 92.

In some embodiments, the AXL variant polypeptide comprises amino acid changes relative to the wild-type AXL sequence (SEQ ID NO: 1) at the following positions: (a) glycine 32; (b) aspartic acid 87; (c) valine 92; (d) glycine 127 and (e) alanine 72.

In some embodiments, the AXL variant polypeptide comprises amino acid changes relative to the wild-type AXL sequence (SEQ ID NO: 1) at the following position: alanine 72.

In some embodiments, in the AXL variant polypeptide glycine 32 residue is replaced with a serine residue, aspartic acid 87 residue is replaced with a glycine residue, valine 92 residue is replaced with an alanine residue, or glycine 127 residue is replaced with an arginine residue or a combination thereof.

In some embodiments, in the AXL variant polypeptide aspartic acid 87 residue is replaced with a glycine residue or valine 92 residue is replaced with an alanine residue or a combination thereof.

In some embodiments, in the AXL variant polypeptide alanine 72 residue is replaced with a valine residue.

In some embodiments, in the AXL variant polypeptide glycine 32 residue is replaced with a serine residue, aspartic acid 87 residue is replaced with a glycine residue, valine 92 residue is replaced with an alanine residue, glycine 127 residue is replaced with an arginine residue or an alanine 72 residue is replaced with a valine residue or a combination thereof.

In some embodiments, the AXL variant comprises amino acid changes relative to the wild-type AXL sequence (SEQ ID NO: 1) at the following positions: (a) glutamic acid 26; (b) valine 79; (c) valine 92; and (d) glycine 127.

In some embodiments, in the AXL variant polypeptide glutamic acid 26 residue is replaced with a glycine residue, valine 79 residue is replaced with a methionine residue, valine 92 residue is replaced with an alanine residue, or glycine 127 residue is replaced with an arginine residue or a combination thereof.

In some embodiments, in the AXL variant polypeptide comprises at least an amino acid region selected from the group consisting of amino acid region 19-437, 130-437, 19-132, 21-121, 26-132, 26-121 and 1-437 of the wild-type AXL polypeptide (SEQ ID NO: 1), and wherein one or more amino acid modifications occur in said amino acid region.

In some embodiments, in the AXL variant polypeptide comprises amino acid changes relative to the wild-type AXL sequence (SEQ ID NO: 1) at the following positions: (a) glycine 32; (b) aspartic acid 87; (c) alanine 72; and valine 92.

In some embodiments, in the AXL variant polypeptide glycine 32 is replaced with a serine residue, aspartic acid 87 is replaced with a glycine residue, alanine 72 is replaced with a valine residue, and valine 92 is replaced with an alanine residue, or a combination thereof.

In some embodiments, the soluble AXL polypeptide is a fusion protein comprising an Fc domain and wherein said AXL variant comprises amino acid changes relative to wild-type AXL sequence (SEQ ID NO:1) at the following positions: (a) glycine 32; (b) aspartic acid 87; (c) alanine 72; and (d) valine 92.

In some embodiments, the soluble AXL polypeptide is a fusion protein comprising an Fc domain and wherein glycine 32 is replaced with a serine residue, aspartic acid 87 is replaced with a glycine residue, alanine 72 is replaced with a valine residue, and valine 92 is replaced with an alanine residue, or a combination thereof.

In some embodiments, the soluble AXL polypeptide is a fusion protein comprising an Fc domain and wherein said AXL variant comprises amino acid changes relative to wild-type AXL sequence (SEQ ID NO:1) at the following positions: (a) glycine 32; (b) aspartic acid 87; (c) alanine 72; (d) valine 92; and (e) glycine 127.

In some embodiments, the soluble AXL polypeptide is a fusion protein comprising an Fc domain and wherein glycine 32 is replaced with a serine residue, aspartic acid 87 is replaced with a glycine residue, alanine 72 is replaced with a valine residue, valine 92 is replaced with an alanine residue, and glycine 127 is replaced with an arginine residue or a combination thereof.

In some embodiments, the soluble AXL polypeptide is a fusion protein comprising an Fc domain, lacks a functional FN domain, and wherein said AXL variant comprises amino acid changes relative to wild-type AXL sequence (SEQ ID NO:1) at the following positions: (a) glycine 32; (b) aspartic acid 87; (c) alanine 72; and (d) valine 92.

In some embodiments, the soluble AXL variant is a fusion protein comprising an Fc domain, lacks a functional FN domain, and wherein glycine 32 is replaced with a serine residue, aspartic acid 87 is replaced with a glycine residue, alanine 72 is replaced with a valine residue, and valine 92 is replaced with an alanine residue, or a combination thereof.

In some embodiments, the soluble AXL polypeptide is a fusion protein comprising an Fc domain, lacks a functional FN domain, and wherein said AXL variant comprises amino acid changes relative to wild-type AXL sequence (SEQ ID NO:1) at the following positions: (a) glycine 32; (b) aspartic acid 87; (c) alanine 72; (d) valine 92; and (e) glycine 127.

In some embodiments, the soluble AXL variant is a fusion protein comprising an Fc domain, lacks a functional FN domain, and wherein glycine 32 is replaced with a serine residue, aspartic acid 87 is replaced with a glycine residue, alanine 72 is replaced with a valine residue, valine 92 is replaced with an alanine residue, and glycine 127 is replaced with an arginine residue or a combination thereof.

In some embodiments, the soluble AXL polypeptide is a fusion protein comprising an Fc domain, lacks a functional FN domain, lacks an Ig2 domain, and wherein said AXL variant comprises amino acid changes relative to wild-type AXL sequence (SEQ ID NO:1) at the following positions: (a) glycine 32; (b) aspartic acid 87; (c) alanine 72 and (d) valine 92.

In some embodiments, the soluble AXL variant is a fusion protein comprising an Fc domain, lacks a functional FN domain, lacks an Ig2 domain and wherein glycine 32 is replaced with a serine residue, aspartic acid 87 is replaced with a glycine residue, alanine 72 is replaced with a valine residue, and valine 92 is replaced with an alanine residue or a combination thereof.

In some embodiments, the soluble AXL polypeptide is a fusion protein comprising an Fc domain, lacks a functional FN domain, lacks an Ig2 domain, and wherein said AXL variant comprises amino acid changes relative to wild-type AXL sequence (SEQ ID NO:1) at the following positions: (a) glycine 32; (b) aspartic acid 87; (c) alanine 72; (d) valine 92; and (e) glycine 127.

In some embodiments, the soluble AXL variant is a fusion protein comprising an Fc domain, lacks a functional FN domain, lacks an Ig2 domain and wherein glycine 32 is replaced with a serine residue, aspartic acid 87 is replaced with a glycine residue, alanine 72 is replaced with a valine residue, valine 92 is replaced with an alanine residue, and glycine 127 is replaced with an arginine residue or a combination thereof.

In some embodiments, the soluble AXL variant polypeptide has an affinity of at least about $1 \times 10^{-8}$ M, $1 \times 10^{-9}$ M, $1 \times 10^{-10}$ M, $1 \times 10^{-11}$ M or $1 \times 10^{-12}$ M for GAS6.

In some embodiments, the soluble AXL variant polypeptide exhibits an affinity to GAS6 that is at least about 5-fold stronger, at least about 10-fold stronger or at least about 20-fold stronger than the affinity of the wild-type AXL polypeptide.

In some embodiments, the soluble AXL, MER or Tyro3 variant polypeptide further comprises a linker. In some embodiments, the linker comprises one or more (GLY)$_4$SER units. In some embodiments, the linker comprises 1, 2, 3 or 5 (GLY)$_4$SER units.

In some embodiments, the soluble AXL MER and/or Tyro3 variant polypeptide inhibits binding between wild-type AXL, MER and/or Tyro3 polypeptide and a GAS6 protein in vivo or in vitro.

In some embodiments, the soluble AXL variant polypeptide is a fusion polypeptide comprising an Fc domain.

DEFINITIONS

In the description that follows, a number of terms conventionally used in the field of cell culture are utilized extensively. In order to provide a clear and consistent understanding of the specification and claims, and the scope to be given to such terms, the following definitions are provided.

"Inhibitors," "activators," and "modulators" of AXL, MER or Tyro3 or its ligand GAS6 are used to refer to inhibitory, activating, or modulating molecules, respectively, identified using in vitro and in vivo assays for receptor or ligand binding or signaling, e.g., ligands, receptors, agonists, antagonists, and their homologs and mimetics.

The terms "polypeptide," "peptide" and "protein" are used interchangeably herein to refer to a polymer of two or more amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms "antibody" and "antibodies" are used interchangeably herein and refer to a polypeptide capable of interacting with and/or binding to another molecule, often referred to as an antigen. Antibodies can include, for example "antigen-binding polypeptides" or "target-molecule binding polypeptides." Antigens of the present invention can include for example any polypeptides described in the present invention.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. All single letters used in the present invention to represent amino acids are used according to recognized amino acid symbols routinely used in the field, e.g., A means Alanine, C means Cysteine, etc. An amino acid is represented by a single letter before and after the relevant position to reflect the change from original amino acid (before the position) to changed amino acid (after position). For example, A19T means that amino acid alanine at position 19 is changed to threonine.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having cancer, including without limitation, adenocarcinoma of the ovary or prostate, breast cancer, glioblastoma, etc., including those who have undergone or are candidates for resection (surgery) to remove cancerous tissue. Subjects may be human, but also include other mammals, particularly those mammals useful as laboratory models for human disease, e.g. mouse, rat, etc.

The definition of an appropriate patient sample encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents; washed; or enrichment for certain cell populations, such as endometrial cells, kidney disease cells, inflammatory disease cells and/or transplant rejection (GVHD) cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's sample cell, e.g., a sample comprising polynucleotides and/or polypeptides that is obtained from a patient's sample cell (e.g., a cell lysate or other cell extract comprising polynucleotides and/or polypeptides); and a sample comprising sample cells from a patient. A biological sample comprising a sample cell from a patient can also include normal, non-diseased cells.

The term "diagnosis" is used herein to refer to the identification of a molecular or pathological state, disease or condition, such as the identification of endometriosis, kidney disease, inflammatory disease and/or transplant rejection (GVHD).

The term "prognosis" is used herein to refer to the prediction of the likelihood of disease-attributable death or progression of endometriosis, kidney disease, inflammatory disease and/or transplant rejection (GVHD). The term "prediction" is used herein to refer to the act of foretelling or estimating, based on observation, experience, or scientific reasoning. In one example, a physician may predict the likelihood that a patient will survive, treating, reducing, or preventing endometriosis, kidney disease, inflammatory disease and/or transplant rejection (GVHD)

As used herein, the terms "treatment," "treating," and the like, refer to administering an agent, or carrying out a procedure (e.g., a surgical procedure, etc.), for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of any metastatic tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. In treating, reducing, or preventing endometriosis, kidney disease, inflammatory disease and/or transplant rejection (GVHD) the inhibitor agent may directly decrease the onset or progression of endometriosis, kidney disease, inflammatory disease and/or transplant rejection (GVHD).

Treating may refer to any indicia of success in the treatment or amelioration or prevention of endometriosis, kidney disease, inflammatory disease and/or transplant rejection (GVHD), including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with endometriosis, kidney disease, inflammatory disease and/or transplant rejection (GVHD). The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic (i.e., first therapeutic agent) and the compounds as used herein. When administered in combination, each component can be administered at the same time or sequentially in any order at different points in time. Thus, each component can be administered separately but sufficiently closely in time so as to provide the desired therapeutic effect. First therapeutic agents contemplated for use with the methods of the present invention include any other agent for use in the treatment of endometriosis, kidney disease, inflammatory disease and/or transplant rejection (GVDH). Examples of such therapeutic agents include but are not limited to Leuprolide acetate, Goserelin, Triptorelin pamoate, Dienogest, Danazol, Medroxyprogesterone acetate, Nafarelin and Buserelin.

"Concomitant administration" of a known therapeutic agent with a pharmaceutical composition of the present invention means administration of the therapeutic agent and inhibitor agent at such time that both the known therapeutic agent and the composition of the present invention will have a therapeutic effect. Such concomitant administration may involve concurrent (i.e. at the same time), prior, or subsequent administration of the drug with respect to the administration of a compound of the present invention. A person of ordinary skill in the art would have no difficulty determining the appropriate timing, sequence and dosages of administration for particular drugs and compositions of the present invention. Therapeutic agents contemplated for concomitant administration according to the methods of the present invention include any other agent for use in the treatment of endometriosis, kidney disease, inflammatory disease and/or transplant rejection (GVDH). Examples of such therapeutic agents include but are not limited to Leuprolide acetate, Goserelin, Triptorelin pamoate, Dienogest, Danazol, Medroxyprogesterone acetate, Nafarelin and Buserelin.

As used herein, the phrase "disease-free survival," refers to the lack of such endometriosis, kidney disease, inflammatory disease and/or transplant rejection (GVHD) recurrence and/or spread and the fate of a patient after diagnosis, with respect to the effects of the endometriosis, kidney disease, inflammatory disease and/or transplant rejection (GVHD) on the life-span of the patient. The phrase "overall survival" refers to the fate of the patient after diagnosis, despite the possibility that the cause of death in a patient is not directly due to the effects of the endometriosis, kidney disease, inflammatory disease and/or transplant rejection (GVHD). The phrases, "likelihood of disease-free survival", "risk of recurrence" and variants thereof, refer to the probability of recurrence or spread in a patient subsequent to diagnosis of endometriosis, kidney disease, inflammatory disease and/or transplant rejection (GVHD), wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

The phrase "determining the treatment efficacy" and variants thereof can include any methods for determining that a treatment is providing a benefit to a subject. The term "treatment efficacy" and variants thereof are generally indicated by alleviation of one or more signs or symptoms associated with the disease and can be readily determined by one skilled in the art. "Treatment efficacy" may also refer to the prevention or amelioration of signs and symptoms of toxicities typically associated with standard or non-standard treatments of a disease. Determination of treatment efficacy is usually indication and disease specific and can include any methods known or available in the art for determining that a treatment is providing a beneficial effect to a patient. For example, evidence of treatment efficacy can include but is not limited to remission of the disease or indication. Further, treatment efficacy can also include general improvements in the overall health of the subject, such as but not limited to enhancement of patient life quality, increase in predicted subject survival rate, decrease in depression or decrease in rate of recurrence of the indication (increase in remission time). (See, e.g., *Physicians' Desk Reference* (2010).)

Kidney disease can include diabetic nephropathy and/or progressive glomerulonephritis. Inflammatory diseases can include liver inflammation, steatohepatitis and liver fibrosis.

DETAILED DESCRIPTION

The present invention is based in part on the discovery that the AXL/GAS6, MER/GAS6 and Tyro3/GAS6 pathways are related to endometriosis, kidney disease, inflammatory disease or transplant rejection (GVHD). AXL, MER, Tyro3 and GAS6, as well as related pathways, have also been described in WO2011/091305, as well as U.S. application Ser. Nos. 13/554,954 and 13/595,936; all of which are incorporated herein by reference in their entireties for all purposes.

The AXL/GAS6, MER/GAS6 and Tyro3/GAS6 pathways are related to endometriosis, kidney disease, inflammatory disease or transplant rejection (GVHD). Accordingly, AXL/GAS6, MER/GAS6 and Tyro3/GAS6 antagonism can be used as therapeutic strategies for treatment, prevention or reduction of endometriosis, kidney disease, inflammatory disease or transplant rejection (GVHD) as well as for improvement of the symptoms of endometriosis, kidney disease, inflammatory disease or transplant rejection (GVHD). As such, the present invention provides compositions and methods useful for treating endometriosis, kidney disease, inflammatory disease and/or transplant rejection (GVHD), and symptoms associated with such diseases, e.g., via inhibition of AXL, MER, Tyro3 and/or GAS6 related pathways. In addition, the present invention provides reagents and methods useful for determining the likelihood of a subject to be susceptible to endometriosis, kidney disease, inflammatory disease and/or transplant rejection (GVHD), e.g., via detecting the level of activity of AXL, MER, Tyro3 and/or GAS6.

In some embodiments, the methods of the present invention can be used for treatment, prevention or reduction of endometriosis and/or improvement of the symptoms associated with endometriosis. Symptoms of endometriosis can include but are not limited to pelvic pain, infertility, dysmenorrhea, ovulatory pain, non menstrual pain, heavy bleeding, urinary symptoms, dyschezia and/or dyspareunia.

In some embodiments, the methods of the present invention can be used for treatment, prevention or reduction of kidney disease and/or improvement of the symptoms associated with kidney disease. Examples of kidney diseases can include but are not limited to diabetic nephropathy and progressive glomerulonephritis. Symptoms of diabetic nephropathy can include but are not limited to edema, proteinuria, fluid accumulation (and accompanied weight gain), hypertension, headache, poor appetite, anorexia, nausea and vomiting, malaise, fatigue, headache, hiccups and/or generalized itching. Symptoms of progressive glomerulonephritis include but are not limited to loss of kidney function, anemia, hematuria, red blood cell casts in the urine, proteinuria, oliguria, fluid retention, hypertension, edema and/or uremia.

In some embodiments, the methods of the present invention can be used for treatment, prevention or reduction of inflammatory diseases. Examples of inflammatory diseases include liver inflammation, steatohepatitis and liver fibrosis. Symptoms of liver inflammation can include flu-like symptoms (including for example malaise, muscle and joint aches, fever, nausea or vomiting, diarrhea, and headache), loss of appetite, aversion to smoking among smokers, dark urine, yellowing of the eyes and skin (i.e., jaundice), abdominal discomfort, tender hepatomegaly, lymphadenopathy, splenomegaly, peripheral edema, bleeding, damage and scarring of liver (i.e., cirrhosis), weight loss and/or ascites (fluid in the abdominal cavity). Acne, abnormal menstruation, lung scarring, inflammation of the thyroid gland and kidneys can occur with autoimmune hepatitis. Symptoms of steatohepatitis can include fatigue, weight loss, weakness, liver inflammation and/or cirrhosis. Symptoms of liver fibrosis can include ascites, hepatic encephalopathy, bleeding from esophageal varices, spider angiomata (spider nevi), palmar erythema, Muehrcke's lines, Terry's nails, clubbing, hypertrophic osteoarthropathy, Dupuytren's contracture, gynecomastia, hypogonadism, enlarge liver, splenomegaly, caput medusa, Cruveilhier-Baumgarten murmur, fetor hepaticus, jaundice, asterixis, weakness, fatigue, anorexia, weight loss, hepatic encephalopathy, hepatocellular carcinoma, portal hypertension, immune system dysfunction, fluid in the abdomen, hepatorenal syndrome, hepatopulmonary syndrome, portopulmonary hypertension and/or portal hypertensive gastropathy.

In some embodiments, the methods of the present invention can be used for treatment, prevention or reduction of transplant rejection (GVHD). Symptoms of transplant rejection can include liver damage, skin rash, mucosa damage, gastrointestinal tract damage, idiopathic pneumonitis, connective tissue damage, exocrine gland damage and mucosal damage to the vagina. Symptoms for GVHD of the gastrointestinal tract can result in severe intestinal inflammation, sloughing of the mucosal membrane, severe diarrhea, abdominal pain, nausea, vomiting. Symptoms of liver GVHD can include increased bilirubin levels. Symptoms of skin GVHD can include maculopapular rash.

AXL, MER and Tyro3 are the three receptor protein tyrosine kinases whose ligand is GAS6. As such, the present invention is based in part on the discovery of inhibitor agents that inhibit and/or antagonize the interaction of the wild-type AXL, MER and/or Tyro3 receptor with the GAS6 ligand and which find use in treating, reducing, or preventing endometriosis, kidney disease, inflammatory disease and/or transplant rejection (GVHD). Such inhibitor agents include those described herein as well as those described in WO2011/091305, as well as U.S. application Ser. Nos. 13/554,954 and 13/595,936; all of which are incorporated herein by reference in their entirety for all purposes.

According to the present invention, inhibitor agents that can be used for treating, reducing, or preventing endometriosis, kidney disease, inflammatory disease and/or transplant rejection (GVHD) can be selected from (a) an inhibitor of AXL, MER and/or Tyro3 activity, (b) an inhibitor of GAS6 activity and (c) an inhibitor of AXL, MER and/or Tyro3-GAS6 interaction, wherein the inhibitor agent is capable of binding to GAS6 with increased affinity compared to wild-type AXL, MER and/or Tyro3.

The present invention also employs soluble AXL, MER and Tyro3 polypeptides for treating, reducing, or preventing endometriosis, kidney disease, inflammatory disease and/or transplant rejection (GVHD). Soluble AXL, MER and Tyro3 polypeptides have a binding activity to GAS6 that is equal to or better than the binding activity of a wild-type AXL polypeptide. In some embodiments of the invention, the soluble AXL, MER or Tyro3 polypeptides are utilized as therapeutic agents.

The present invention also provides a method of determining treatment efficacy of administering an inhibitor agent comprising detecting the level of AXL, MER, Tyro3 and/or GAS6 activity in a biological sample from a subject treated with said inhibitor agent, wherein a decrease in AXL, MER, Tyro3 and/or GAS6 activity is indicative of the efficacy of treatment with the inhibitor agent. In some embodiments, the level is compared to a predetermined, standard level.

Predetermined standard levels of AXL, MER, Tyro3 and/or GAS6 activity can be defined using a variety of methods known to those of skill in the art. Generally, standard levels are determined by determining the level of AXL, MER, Tyro3 and/or GAS6 activity in a sufficiently large number of samples obtained from normal, healthy control subjects. Further, standard level information can be obtained from publically available databases, as well as other sources. (See, e.g., Bunk, D. M., "Reference Materials and Reference Measurement Procedures: An Overview from a National Metrology Institute," *Clin. Biochem. Rev.,* 28(4):131-137 (2007); Suraj Peril, et al., "Development of Human Protein Reference Database as an Initial Platform for Approaching Systems Biology in Humans" *Genome Res.* 13: 2363-2371 (2003); *Remington: The Science and Practice of Pharmacy,* Twenty First Edition (2005).) In some embodiments, an increase or decrease of the level of AXL, MER, Tyro3 and/or GAS6 activity in a sample obtained from a subject treated with an inhibitor agent of the present invention is determined by comparing the level of AXL, MER, Tyro3 and/or GAS6 activity to a predetermined standard level.

The present invention also provides a method for determining the treatment regimen of an inhibitor agent comprising detecting the level of AXL, MER, Tyro3 and/or GAS6 activity in a biological sample from a subject treated with said inhibitor agent, and determining a treatment regimen of the inhibitor agent based on an increase or decrease in the level of AXL, MER, Tyro3 and/or GAS6 activity. In some embodiments, the level is compared to a predetermined, standard level.

Information regarding the increase or decrease in the level of AXL, MER, Tyro3 and/or GAS6 activity can be used to determine the treatment efficacy of treatment with an inhibitor agent of the present invention, as well as to tailor treatment regimens for treatment with an inhibitor agent of the present invention. In some embodiments the level of AXL, MER, Tyro3 and/or GAS6 activity can be used to determine whether to continue treatment with the inhibitor agent. In other embodiments the level of AXL, MER, Tyro3 and/or GAS6 activity can be used to determine whether to discontinue treatment with the inhibitor agent. In other embodiments the level of AXL, MER, Tyro3 and/or GAS6 activity can be used to determine whether to modify treatment with the inhibitor agent. In other embodiments the level of AXL, MER, Tyro3 and/or GAS6 activity can be used to determine whether to increase or decrease the dosage of the inhibitor agent that is administered. In other embodiments the level of AXL, MER, Tyro3 and/or GAS6 activity can be used to determine whether to change the dosing frequency for the inhibitor agent. In further embodiments, the level of AXL, MER, Tyro3 and/or GAS6 activity can be used to determine whether to change the number of dosages per day, per week, times per day. In yet further embodiments the level of AXL, MER, Tyro3 and/or GAS6 activity can be used to determine whether to change the dosage amount.

According to yet another aspect of the invention, it provides methods for treating, reducing or preventing endometriosis, kidney disease, inflammatory disease and/or transplant rejection (GVHD). In some embodiments, methods of the present invention include inhibiting the activity of AXL, MER, Tyro3 and/or the activity of GAS6, or the interaction between AXL, MER and/or Tyro3 and GAS6. For example, the activity of AXL, MER, Tyro3 and/or GAS6 can be inhibited at the gene expression level, mRNA processing level, translation level, post-translation level, protein activation level, etc. In some other examples, the activity of AXL, MER, Tyro3 or GAS6 can be inhibited by small molecules, biological molecules, e.g., polypeptides, polynucleotides, antibodies, antibody drug conjugates, etc. In some other examples, the activity of AXL, MER, Tyro3 or GAS6 can be inhibited by one or more AXL, MER or Tyro3 variant polypeptides or isolated antibodies of the present invention.

According to yet another aspect of the invention, it provides methods for determining the susceptibility of a subject to endometriosis, kidney disease, inflammatory disease and/or transplant rejection (GVHD) by detecting and/or determining the level of AXL, MER and/or Tyro3 activity or GAS6 activity in a biological sample from a subject of interest. In some embodiments, the level of AXL, MER and/or Tyro3 activity or GAS6 activity is measured by the level of mRNA expression, the level of protein expression, the level of protein activation or any suitable indicator corresponding to the activity of AXL, MER and/or Tyro3 or GAS6 either directly or indirectly. In some embodiments, the level of AXL, MER and/or Tyro3 activity or GAS6 activity in a biological sample is further compared to a predetermined level, e.g., standard level obtained by establishing normal levels or ranges of AXL, MER and/or Tyro3 activity or GAS6 activity based on a population of samples from individuals that do not develop or have not developed endometriosis, kidney disease, inflammatory disease and/or transplant rejection (GVHD) or from normal tissues. For example, an increase of AXL, MER and/or Tyro3 activity or GAS6 activity over the predetermined level or standard level is indicative of a predisposition of the subject to develop endometriosis, kidney disease, inflammatory disease and/or transplant rejection (GVHD).

In yet another aspect of the invention, it provides methods for treating, reducing or preventing endometriosis, kidney disease, inflammatory disease and/or transplant rejection (GVHD) by inhibiting AXL, MER or Tyro3 signaling. In some embodiments, the methods of the present invention provide for inhibiting AXL, MER or Tyro3 activation. In some embodiments, the present invention provides for inhibiting AXL, MER or Tyro3 pathways. AXL, MER or Tyro3 pathways can include but are not limited to the PI3K/AKT pathway, the MAPK pathway and/or the cell motility pathway (involving for example ACTN4). In some embodiments, the present invention provides for inhibiting members of the AXL pathways, e.g., members of the PI3K/AKT pathway, the MAPK pathway and/or the cell motility pathway. Members of the PI3K/AKT pathway can include for example but are not limited to PTEN, PI3K, AKT, TSC2 and mTOR. Members of the MAPK pathway can include for example but are not limited to Ras, Raf, MEK and Erk. Members of the cell motility pathway can include for example but are not limited to ACTN4.

In some embodiments, the inhibitor agent binds to two or more epitopes on a single GAS6 molecule. The two or more epitopes can include at least one of the major and/or minor AXL, MER and/or Tyro3 binding site on GAS6. In some embodiments, the epitopes are separate or distinct epitopes. In some embodiments the epitopes overlap. In some embodiments, the epitopes do not overlap. In some embodiments, the epitopes are adjacent. In some embodiments, the epitopes are not adjacent. In some embodiments, the epitopes include the major and/or minor AXL, MER and/or Tyro3 binding site on GAS6. These GAS6 epitopes of the present invention, and to which the inhibitor agents of the present invention bind, can be located on one or more GAS6 molecules. In some embodiments, the epitopes are located on a single GAS6 molecule.

In some embodiments, the inhibitor agent is capable of binding to the major and/or minor AXL, MER and/or Tyro3 binding sites on a single GAS6. In some embodiments, the inhibitor agent is capable of binding the major AXL, MER and/or Tyro3 binding site of GAS6 and one or more additional GAS6 epitopes. In other embodiments, the inhibitor agent is capable of binding to the AXL, MER and/or Tyro3 minor binding site on GAS6 and one or more additional epitopes. In some other embodiments, the inhibitor agent is capable of binding two or more distinct epitopes on GAS6. The additional GAS6 epitopes can include any epitopes on GAS6 which lead to increased affinity and/or increased avidity of the inhibitor agent binding to GAS6 as compared to wild-type AXL, MER and/or Tyro3. In some embodiments, the AXL, MER and/or Tyro3 variant polypeptides of the present invention bind two epitopes on a single GAS6 molecule. In some embodiments, the two epitopes are the major and minor AXL, MER and/or Tyro3 binding sites.

According to the invention, GAS6 receptors include AXL, MER and Tyro3. The inhibitor agents of the present invention can also in some embodiments antagonize the major and/or minor GAS6/receptor interaction. In some embodiments, the inhibitor agent is capable of antagonizing the major and/or minor GAS6/receptor binding interaction. In other embodiments, the inhibitor agent is capable of antagonizing the major GAS6/receptor binding interaction (e.g., interfering with and/or inhibiting the major GAS6/receptor binding interaction). In some embodiments, the inhibitor agent is capable of antagonizing the minor GAS6/receptor binding interaction (e.g., interfering with and/or inhibiting the minor GAS6/receptor binding interaction).

Inhibitor agents can also include for example protein scaffolds (i.e., smaller proteins that are capable of achieving comparable affinity and specificity using molecular structures that can be for example one-tenth the size of full antibodies).

The inhibitor agents can also include non-antibody polypeptides. In some embodiments, the inhibitor agent is a non-antibody polypeptide. In some embodiments, the non-antibody polypeptide can include but is not limited to peptibodies, darpins, avimers, adnectins, anticalins, affibodies, maxibodies, or other protein structural scaffold, or a combination thereof.

In some embodiments the inhibitor agent provided by the present invention is an AXL, MER and/or Tyro3 variant polypeptide, e.g., an AXL, MER and/or Tyro3 variant polypeptide that has a binding activity to GAS6 that is substantially equal to or better than the binding activity of a wild-type AXL, MER and/or Tyro3 polypeptide. In some embodiments of the present invention, the AXL, MER and/or Tyro3 variant polypeptides are utilized as therapeutic agents.

The AXL protein, with reference to the native sequence of SEQ ID NO: 1, comprises an immunoglobulin (Ig)-like domain from residues 27-128, a second Ig-like domain from residues 139-222, fibronectin type 3 domains from residues 225-332 and 333-427, intracellular domain from residues 473-894 including tyrosine kinase domain. The tyrosine residues at 779, 821 and 866 become autophosphorylated upon receptor dimerization and serve as docking sites for intracellular signaling molecules. The native cleavage site to release the soluble form of the polypeptide lies at residues 437-451.

For the purposes of the invention, a soluble form of AXL (soluble AXL, sAXL or sAXL polypeptide) includes both wild-type AXL and AXL variant polypeptides and is the portion of the polypeptide that is sufficient to bind GAS6 at a recognizable affinity, e.g., high affinity, which normally lies between the signal sequence and the transmembrane domain, i.e. generally from about SEQ ID NO: 1 residue 19-437, but which may comprise or consist essentially of a truncated version of from about residue 19, 25, 30, 35, 40, 45, 50 to about residue 132, 450, 440, 430, 420, 410, 400, 375, 350, to 321, e.g., residue 19-132. According to the methods of the present invention, SEQ ID NO:1 can be used interchangeably with amino acids 8-894 of SEQ ID NO: 1, both of which refer to the wild-type AXL sequence. In some embodiments, a soluble form of AXL lacks the transmembrane domain, and optionally the intracellular domain.

In some embodiments, the inhibitor agent is an AXL variant polypeptide that lacks the AXL transmembrane domain and has at least one mutation relative to wild-type that increases affinity of the AXL polypeptide binding to GAS6 as compared to wild-type GAS6.

The MER protein, with reference to the native SEQ ID NO:2, comprises an immunoglobulin (Ig)-like domain from residues 81-186, a second Ig-like domain from residues 197-273, fibronectin type 3 domains from residues 284-379 and 383-482, intracellular domain from residues 527-999 including tyrosine kinase domain. The tyrosine residues at 749, 753, 754 and 872 become autophosphorylated upon receptor dimerization and serve as docking sites for intracellular signaling molecules.

For the purposes of the invention, a soluble form of MER (sMER) is the portion of the polypeptide that is sufficient to bind GAS6 at a recognizable affinity, e.g., high affinity, which normally lies between the signal sequence and the transmembrane domain, i.e. generally from about SEQ ID NO: 2 residue 21-526, but which may comprise or consist essentially of a truncated version In some embodiments, a soluble form of MER lacks the transmembrane domain (i.e., generally from about SEQ ID NO: 2 residue 506-526), and optionally the intracellular domain (i.e., generally from about SEQ ID NO: 2 residue 527-999).

In some embodiments, the inhibitor agent is a soluble MER variant polypeptide wherein said MER polypeptide lacks the MER transmembrane domain and has at least one mutation relative to wild-type that increases affinity of the MER polypeptide binding to GAS6 as compared to wild-type MER.

The Tyro3 protein, with reference to the native SEQ ID NO:3, comprises an immunoglobulin (Ig)-like domain from residues 41-128, a second Ig-like domain from residues 139-220, fibronectin type 3 domains from residues 225-317 and 322-413, intracellular domain from residues 451-890 including tyrosine kinase domain. The tyrosine residues at 681, 685, 686 and 804 become autophosphorylated upon receptor dimerization and serve as docking sites for intracellular signaling molecules.

For the purposes of the invention, a soluble form of Tyro3 (sTyro3) is the portion of the Tyro3 polypeptide that is sufficient to bind GAS6 at a recognizable affinity, e.g., high affinity, which normally lies between the signal sequence and the transmembrane domain, i.e. generally from about SEQ ID NO: 3 residue 41-450, but which may comprise or consist essentially of a truncated version In some embodiments, a soluble form of AXL lacks the transmembrane domain (i.e., generally from about SEQ ID NO: 3 residue 430-450), and optionally the intracellular domain (i.e., generally from about SEQ ID NO: 3 residue 451-890).

In some embodiments, the inhibitor agent is a soluble Tyro3 variant polypeptide wherein said Tyro3 polypeptide lacks the Tyro3 transmembrane domain and has at least one mutation relative to wild-type Tyro3 that increases affinity of the Tyro3 polypeptide binding to GAS6 as compared to wild-type Tyro3.

In some embodiments, the AXL, MET or Tyro3 variant polypeptide lacks the AXL, MET or Tyro3 transmembrane domain and is a soluble variant polypeptide, e.g., polypeptides (sAXL, sMER or sTyro3 variant polypeptide).

In some embodiments, the AXL, MER or Tyro3 variant polypeptide lacks the AXL, MER or Tyro3 intracellular domain.

In some embodiments, the inhibitor agent of the present invention inhibits binding between a wild-type AXL, MER and/or Tyro3 polypeptide and a GAS6 protein in vivo or in vitro. In some embodiments, the AXL, MER or Tyro3 variant polypeptide inhibits binding between a wild-type AXL, MER and/or Tyro3 polypeptide and a GAS6 protein in vivo or in vitro.

The inhibitor agents of the present invention can also exhibit an enhanced or better pharmacokinetic profile. In some embodiments, the enhanced or better pharmacokinetic profile includes for example but is not limited to a better absorption profile, better distribution profile, better metabolism profile, better excretion profile, better liberation profile, increased half-life, decrease half-life, faster rate of action, longer duration of effect as compared to AXL, MER and/or Tyro3 wild-type polypeptides which do not lack a transmembrane domain. One of skill in the art would understand preferred pharmacokinetic profile parameters for particular needs including for example treatment regimens, and how to appropriately implement such parameters in treatment regimens.

The wild-type AXL, MER and Tyro3 all contain two fibronectin domains. In some embodiments, the AXL, MER and Tyro3 polypeptides of the invention lack a functional fibronectin (FN) domain. Lacks or lacking a functional fibronectin domain can include but is not limited to deletion of one or both fibronectin domains and/or introducing mutations that inhibit, reduce or remove the functionality of one or both fibronectin domains, where such mutations can include for example but are not limited to substitution, deletion and insertion mutations. In some embodiments, the polypeptides of the invention have fibronectin 1 (FN1) deleted, fibronectin 2 (FN2) deleted, or FN1 and FN 2 both deleted. In some embodiments, the polypeptides of the invention have portions of FN1 mutated and/or deleted, FN2 mutated and/or deleted, or FN1 and FN2 mutated and/or deleted.

In some embodiments, the AXL, MER or Tyro3 variant polypeptide lacks a functional AXL, MER or Tyro3 fibronectin (FN) domain. In some embodiments, the AXL, MER or Tyro3 variant polypeptide exhibits increased affinity of the polypeptide binding to GAS6 as compared to wild-type AXL, MER and/or Tyro3. In some embodiments, the AXL, MER or Tyro3 variant polypeptide lacks a functional fibronectin (FN) domain also exhibits increased affinity of the polypeptide binding to GAS6 as compared to wild-type AXL, MER and/or Tyro3.

In some embodiments, the lack of a functional fibronectin domain results in increased affinity of the AXL, MER or Tyro3 polypeptide binding to GAS6. In some embodiments, the lack of a functional fibronectin domain results in an enhanced or better pharmacokinetic profile, including for example but not limited to a better absorption profile, better distribution profile, better metabolism profile, better excretion profile, better liberation profile, increased half-life, decreased half-life, faster rate of action, longer duration of effect as compared to other wild-type polypeptides or other polypeptides which do not lack a functional fibronectin domain. One of skill in the art would understand preferred pharmacokinetic profile parameters for particular needs including for example treatment regimens, and how to appropriately implement such parameters in treatment regimens.

In some embodiments, the AXL, MER or Tyro3 variant polypeptide lacks the transmembrane domain and has more than one Ig1 domain and exhibits increased affinity of the AXL, MER or Tyro3 polypeptide binding to GAS6 as compared to wild-type AXL, MER and/or Tyro3. In some embodiments, the AXL, MER or Tyro3 polypeptide has two Ig1 domains. In some embodiments, the AXL, MER or Tyro3 polypeptide has three Ig1 domains. In some embodiments, the AXL, MER or Tyro3 polypeptide has more than one Ig1 domain and/or more than one Ig2 domain. In some embodiments, the AXL, MER or Tyro3 polypeptide has two Ig2 domains. In some embodiments, the AXL, MER or Tyro3 polypeptide has two Ig1 domains and 2 Ig2 domains. In some embodiments, the AXL, MER or Tyro3 polypeptide includes for example but is not limited to one of the following Ig domain configurations, as well as any combinations or variations thereof:

Ig1
Ig1-Ig2
Ig1-Ig1
Ig1-Ig1-Ig1
Ig1-Ig2-Ig1
Ig1-Ig2-Ig1-Ig2

In some embodiments, the AXL, MER or Tyro3 polypeptide also lacks the AXL, MER or Tyro3 transmembrane domain and/or exhibits increased affinity of the AXL, MER or Tyro3 polypeptide binding to GAS6. In some embodiments, the AXL, MER or Tyro3 variant polypeptide lacks the transmembrane domain, has more than one Ig1 domain, has more than one Ig2 domain and exhibits increased affinity of the AXL, MER or Tyro3 polypeptide binding to GAS6 as compared to wild-type AXL, MER and/or Tyro3.

In some embodiments, the AXL, MER or Tyro3 has the immunoglobulin domains connected directly to one another. In some embodiments, the AXL, MER or Tyro3 has the immunoglobulin domains connected indirectly, e.g., through a linker molecule including for example any amino acid linker known in the art.

In some embodiments, the one or more AXL, MER or Tyro3 Ig1 and/or 1 or more AXL, MER or Tyro3 Ig2 domains result in an enhanced or better pharmacokinetic profile, including for example but not limited to a better absorption profile, better distribution profile, better metabolism profile, better excretion profile, better liberation profile, increased half-life, decreased half-life, faster rate of action, longer duration of effect as compared to other wild-type polypeptides or other polypeptides which do not lack a functional fibronectin domain. One of skill in the art would understand preferred pharmacokinetic profile parameters for particular needs including for example treatment regimens, and how to appropriately implement such parameters in treatment regimens.

In some embodiments, the AXL, MER or Tyro3 variant polypeptide lacks the AXL, MER or Tyro3 transmembrane domain and is capable of binding two or more epitopes on a single GAS6. In some embodiments, the AXL, MER or Tyro3 variant polypeptide lacks the AXL, MER or Tyro3 transmembrane domain and is capable of binding both the major and minor AXL, MER and/or Tyro3 binding sites on a single GAS6. In some embodiments, the binding of both the major and minor AXL, MER and/or Tyro3 binding is simultaneous. In some embodiments, the binding of both the major and minor AXL, MER and/or Tyro3 binding sites is simultaneous on a single GAS6.

The present invention also provides AXL, MER or Tyro3 variant polypeptides that do not bind two epitopes on a single GAS6 molecule. The present invention also provides AXL, MER or Tyro3 variant polypeptides that do not bind two epitopes on a single GAS6 molecule simultaneously. In some embodiments, the AXL, MER and/or Tyro3 variant polypeptide is not capable of binding two epitopes on a single GAS6, this includes for example monomeric AXL, MER and/or Tyro3 variant polypeptides. In some embodiments, the monomeric AXL, MER or Tyro3 variant polypeptide comprises one Ig1 domain. In some embodiments, the monomeric AXL, MER and/or Tyro3 variant polypeptide is an Fc fusion polypeptide that does not bind to more than one site on a singe Gas6 molecule simultaneously. In some embodiments, the monomeric AXL, MER and/or Tyro3 variant polypeptide that is not capable of binding two epitopes on a single GAS6 comprises two AXL, MER and/or Tyro3 variant polypeptides each of which are not capable of binding two epitopes on a single GAS6 simultaneously. In some embodiments, the monomeric AXL, MER and/or Tyro3 variant polypeptide that is not capable of simultaneously binding two epitopes on a single GAS6 has one Ig1 domain. In some embodiments, the monomeric AXL, MER and/or Tyro3 variant polypeptide that is not capable of simultaneously binding two epitopes on a single GAS6 has an altered half-life when compared to AXL, MER and/or Tyro3 variant polypeptides that are capable of binding two epitopes on a single GAS6. In some embodiments, the polypeptide has one Ig1 domain and lacks a functional Ig2 domain. In some embodiments, the Ig1 domain comprises amino acids 1-131 of AXL (SEQ ID NO:1). In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, has one Ig1 domain, lacks a functional Ig2 domain and wherein said AXL, MER or Tyro3 variant polypeptide exhibits increased affinity of the AXL, MER or Tyro3 variant polypeptide binding to GAS6 compared to wild-type AXL, MER or Tyro3. In some embodiments, the polypeptide of any of the preceding claims, wherein the polypeptide is a soluble AXL, MER or Tyro3 variant polypeptide, wherein said soluble AXL, MER or Tyro3 variant polypeptide lacks the AXL, MER or Tyro3 transmembrane domain, lacks a functional fibronectin (FN) domain, has one Ig1 domain, lacks a functional Ig2 domain and wherein said AXL, MER or Tyro3 variant polypeptide exhibits increased affinity of the AXL, MER or Tyro3 variant polypeptide binding to GAS6 compared to wild-type AXL, MER or Tyro3.

The wild-type AXL, MER and Tyro3 all contain an Ig2 domain. In some embodiments, the AXL, MER and Tyro3 polypeptides of the invention lack a functional Ig2 domain. Lacks or lacking a functional Ig2 domain can include but is not limited to deletion of the Ig2 domain and/or introduction of mutations that inhibit, reduce or remove the functionality of the Ig2 domain, where such mutations can include for example but are not limited to substitution, deletion and insertion mutations. In some embodiments, the polypeptides of the invention lack a functional Ig2 domain. In some embodiments, the polypeptides of the invention lack a functional Ig2 domain and have a wild-type AXL, MER and/or Tyro3 Ig1 domain. In some embodiments, the polypeptides of the invention lack a functional Ig2 domain and have one or more mutations in the Ig1 domain relative to the wild-type AXL, MER and/or Tyro3 Ig1 domain.

In some embodiments, the AXL, MER and/or Tyro3 variant polypeptide includes a linker. A wide variety of linkers are known in the art and any known linker can be employed with the methods of the present invention. In some embodiments, the AXL, MER or Tyro3 variant polypeptide includes one or more linkers or linker units. In some embodiments, the linker is an amino acid linker, including an amino acid sequence of 2, 3, 4 or 5 amino acids which are different that the wild-type AXL, MER and/or Tyro3 sequences. In some embodiments, the linker has 1, 2, 3, 4, 5, 6, 7, 8, 9, 10 or more units. In some embodiments, the linker is (GLY)$_4$SER (SEQ ID NO:10). In some embodiments, the linker has 1, 2, 3, 4, 5, 6, 7, 8, 9, 10 or more (GLY)$_4$SER units. In some embodiments, the linker has 1, 2, 3 or 5 (GLY)$_4$SER units. In some embodiments, the linkers are between the AXL, MER or Tyro3 variant polypeptide and the Fc portion of a fusion polypeptide. In some embodiments, the linkers are between the AXL, MER or Tyro3 variant polypeptide and the Fc portion of a fusion polypeptide and the AXL, MER or Tyro3 variant polypeptide lacks a functional fibronectin domain.

In some embodiments, AXL, MER and/or Tyro3 variant polypeptides of the present invention also include one or more amino acid modifications within the soluble form of wild-type AXL, MER and/or Tyro3, e.g., one or more amino acid modifications that increase its affinity for GAS6. According to the present invention, amino acid modifications include any naturally occurring or man-made amino acid modifications known or later discovered in the field. In some embodiments, amino acid modifications include any naturally occurring mutation, e.g., substitution, deletion, addition, insertion, etc. In some other embodiments, amino acid modifications include replacing existing amino acid with another amino acid, e.g., a conservative equivalent thereof. In yet some other embodiments, amino acid modifications include replacing one or more existing amino acids with non-natural amino acids or inserting one or more non-natural amino acids. In still some other embodiments, amino acid modifications include at least 1, 2, 3, 4, 5, or 6 or 10 amino acid mutations or changes.

In some exemplary embodiments, one or more amino acid modifications can be used to alter properties of the soluble form of AXL, MER and/or Tyro3 e.g., affecting the stability, binding activity and/or specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet. 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

In some embodiments, AXL variant polypeptides, including for example sAXL variants, of the present invention include one or more amino acid modifications within one or more regions of residue 18 to 130, residue 10 to 135, residue 15 to 45, residue 60 to 65, residue 70 to 80, residue 85 to 90, residue 91 to 99, residue 104 to 110, residue 111 to 120, residue 125 to 130, residue 19 to 437, residue 130 to 437, residue 19 to 132, residue 21 to 132, residue 21 to 121, residue 26 to 132, or residue 26 to 121 of wild-type AXL (SEQ ID NO: 1). In some other embodiments, AXL variant polypeptides of the present invention include one or more amino acid modifications within one or more regions of residue 20 to 130, residue 37 to 124 or residue 141 to 212 of wild-type AXL (SEQ ID NO: 1). In yet some other embodiments, variants of the present invention include one or more amino acid modifications at one or more positions of position 19, 23, 26, 27, 32, 33, 38, 44, 61, 65, 72, 74, 78, 79, 86, 87, 88, 90, 92, 97, 98, 105, 109, 112, 113, 116, 118, 127, or 129 of wild-type AXL (SEQ ID NO: 1).

In yet some other embodiments, AXL polypeptide variants of the present invention include one or more amino acid modifications including without any limitation 1) A19T, 2) T23M, 3) E26G, 4) E27G or E27K, 5) G32S, 6) N33S, 7) T38I, 8) T44A, 9) H61Y, 10) D65N, 11) A72V, 12) S74N, 13) Q78E, 14) V79M, 15) Q86R, 16) D87G, 17) D88N, 18) I90M or I90V, 19) V92A, V92G or V92D, 20) I97R, 21) T98A or T98P, 22) T105M, 23) Q109R, 24) V112A, 25) F113L, 26) H116R, 27) T118A, 28) G127R or G127E, and 29) E129K and a combination thereof.

In yet some other embodiments, AXL variant polypeptides of the present invention include one or more amino acid modifications at position 32, 87, 92, or 127 of wild-type AXL (SEQ ID NO: 1) or a combination thereof, e.g., G32S; D87G; V92A and/or G127R. In yet some other embodiments, AXL polypeptide variants of the present invention include one or more amino acid modifications at position 26, 79, 92, 127 of wild-type AXL (SEQ ID NO: 1) or a combination thereof, e.g., E26G, V79M; V92A and/or G127E. In yet some other embodiments, AXL variant polypeptides of the present invention include one or more amino acid modifications at position 32, 87, 92, 127 and/or 72 of wild-type AXL (SEQ ID NO: 1) or a combination thereof, e.g., G32S; D87G; V92A; G127R and/or A72V. In yet some other embodiments, AXL variant polypeptides of the present invention include one or more amino acid modifications at position 87, 92 and/or 127 of wild-type AXL (SEQ ID NO: 1) or a combination thereof, e.g., D87G; V92A; and/or G127R. In yet some other embodiments, AXL variant polypeptides of the present invention include one or more amino acid modifications at position 32, 92, and/or 127 of wild-type AXL (SEQ ID NO: 1) or a combination thereof, e.g., G32S; V92A; and/or G127R. In yet some other embodiments, AXL variant polypeptides of the present invention include one or more amino acid modifications at position 32, 87 and/or 127 of wild-type AXL (SEQ ID NO: 1) or a combination thereof, e.g., G32S; D87G; and/or G127R. In yet some other embodiments, AXL polypeptide variants of the present invention include one or more amino acid modifications at position 32, 87 and/or 92 of wild-type AXL (SEQ ID NO: 1) or a combination thereof, e.g., G32S; D87G; and/or V92A. In yet some other embodiments, AXL variant polypeptides of the present invention include one or more amino acid modifications at position 26, 79, 92, 127 of wild-type AXL (SEQ ID NO: 1) or a combination thereof, e.g., E26G, V79M; V92A and/or G127E. In yet some other embodiments, AXL variant polypeptides of the present invention include one or more amino acid modifications at position 87 and 92 of wild-type AXL (SEQ ID NO: 1) or a combination thereof, e.g., D87G and V92A. In yet some other embodiments, AXL variant polypeptides of the present invention include at least one amino acid modification at position 72 of wild-type AXL (SEQ ID NO: 1), e.g., A72V.

According to the present invention, the inhibitor agent can include but is not limited to a polypeptide, a polypeptide-carrier fusion, a polypeptide-Fc fusion, polypeptide-conjugate, a polypeptide-drug conjugate, an antibody, a bispecific antibody, an antibody-drug conjugate, an antibody fragment, an antibody-related structure, or a combination thereof.

The inhibitor agents of the present invention can include peptides or polypeptides. The peptides and polypeptides of the present invention can include natural and/or synthetic polypeptides. Synthetic polypeptides and methods of making synthetic polypeptides are well known in the art and any known methods for making synthetic polypeptides can be employed with the methods of the present invention. In some embodiments, the inhibitor agent is a natural or synthetic polypeptide. In some embodiments, the inhibitor agent is a natural or synthetic polypeptide-fusion. In some embodiments, the inhibitor agent is a natural or synthetic polypeptide-Fc fusion. In some embodiments the natural or synthetic polypeptide-fusion is a fusion with another protein structural class or scaffold or a natural or synthetic polypeptide-fusion with a polymer or hydrogel or related structure.

According to the present invention, the AXL, MER or Tyro3 variant polypeptides of the present invention can be further modified, e.g., joined to a wide variety of other oligopeptides or proteins for a variety of purposes. For instance, various post-translation or post-expression modifications can be carried out with respect to AXL, MER or Tyro3 variant polypeptides of the present invention. For example, by employing the appropriate coding sequences, one may provide farnesylation or prenylation. In some embodiments, the AXL, MER or Tyro3 variant polypeptides of the present invention can be PEGylated, where the polyethyleneoxy group provides for enhanced lifetime in the blood stream. The AXL, MER or Tyro3 variant polypeptides of the present invention can also be combined with other proteins, such as the Fc of an IgG isotype, which can be complement binding, with a toxin, such as ricin, abrin, diphtheria toxin, or the like, or with specific binding agents that allow targeting to specific moieties on a target cell. The inhibitor agents of the present invention can include polypeptide conjugates and antibody-conjugates. In some embodiments, the inhibitor agent is a polypeptide-conjugate or antibody-conjugate. In some embodiments, the polypeptide conjugate is a drug conjugate. In some embodiments, the peptide or polypeptide conjugate is an antibody-drug conjugates. In some embodiments, the polypeptide conjugate is a polymer conjugate. Polymers of the present invention include but are not limited to PEG, PEG-containing polymers, degradable polymers, biocompatible polymers, hydrogels, as well as other polymer structures that could be conjugated to a polypeptide, and can include combinations thereof.

In some embodiments, the AXL, MER or Tyro3 variant polypeptide of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some other embodiments, the second polypeptide is part or whole of Fc region. In some other embodiments, the second polypeptide is any suitable polypeptide that is substantially similar to Fc, e.g., providing increased size and/or additional binding or interaction with Ig molecules. In some embodiments, the sAXL-Fc fusion molecule is a soluble molecule. In some embodiments, the sAXL-Fc fusion has enhanced affinity toward GAS6. In some embodiments, the sAXL-Fc fusion is a soluble molecule that has enhanced affinity toward GAS6. In some other embodiments, the second polypeptide is any suitable polypeptide that is substantially similar to Fc, e.g., providing increased size and/or additional binding or interaction with Ig molecules. In yet some other embodiments, the second polypeptide is part or whole of an albumin protein, e.g., a human serum albumin protein. In some embodiments, the second polypeptide is a protein or peptide that binds to albumin.

In some other embodiments, the second polypeptide is useful for handling the AXL, MER or Tyro3 variant polypeptides, e.g., purification of AXL, MER or Tyro3 variant polypeptides or for increasing its stability in vitro or in vivo. For example, AXL, MER or Tyro3 variant polypeptides of the present invention can be combined with parts of the constant domain of immunoglobulins (IgG), resulting in chimeric or fusion polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. EP A 394,827; Traunecker et al., Nature, 331: 84-86, 1988. Fusion proteins having disulfide-linked dimeric structures (due to the IgG) can also be more efficient in binding and neutralizing other molecules, than the monomeric secreted protein or protein fragment alone. Fountoulakis et al., J. Biochem. 270: 3958-3964, 1995.

In yet some other embodiments, the second polypeptide is a marker sequence, such as a peptide which facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984.

In still some other embodiments, the second polypeptide is an entity useful for improving the characteristics of AXL, MER or Tyro3 polypeptide variants of the present invention. For instance, a region of additional amino acids, particularly charged amino acids, may be added to the N-terminus of the polypeptide to improve stability and persistence during purification from the host cell or subsequent handling and storage. Also, peptide moieties may be added to the AXL, MER or Tyro3 polypeptide variants of the present invention to facilitate purification and subsequently removed prior to final preparation of the polypeptide. The addition of peptide moieties to facilitate handling of polypeptides are familiar and routine techniques in the art.

In still yet some embodiments, AXL, MER or Tyro3 variant polypeptides of the present invention have a binding activity to GAS6 that is at least equal or better than the wild-type AXL, MER or Tyro3. In some other embodiments, AXL, MER or Tyro3 variant polypeptides of the present invention has a binding activity or affinity to GAS6 that is at least 1-fold, 2-fold, 3-fold, 4-fold, 5-fold, or 6-fold greater than that of the wild-type AXL, MER or Tyro3. In some other embodiments, AXL, MER or Tyro3 polypeptide variant of the present invention has a binding activity or affinity to GAS6 of at least about $1\times10^{-6}$, $1\times10^{-7}$, $1\times10^{-8}$ or $1\times10^{-9}$ M, $1\times10^{-10}$M, $1\times10^{-11}$M or $1\times10^{-12}$M. In yet some other embodiments, sAXL polypeptides of the present invention is capable of inhibiting, inhibit or compete with wild-type AXL binding to GAS6 either in vivo, in vitro or both. In yet some other embodiments, sAXL polypeptides of the present invention inhibit or compete with the binding of AXL S6-1, AXL S6-2, and/or AXL S6-5 (as described in WO2011/091305). In yet some other embodiments, sAXL polypeptides of the present invention inhibit or compete with the binding of any sAXL variant as described in WO2011/091305.

The inhibitor agents of the present invention bind to GAS6 with increased affinity. In some embodiments, the AXL, MER or Tyro3 variant polypeptide exhibits increased affinity of the AXL, MER or Tyro3 polypeptide binding to GAS6 as compared to wild-type AXL, MER or Tyro3. In some embodiments, AXL, MER or Tyro3 variant polypeptide exhibits an affinity to GAS6 that is at least about 5-fold stronger, at least about 10-fold stronger or at least about 20-fold stronger, 50-fold stronger, 100-fold stronger or at least 200-fold stronger, etc. than the affinity of the wild-type AXL, MER or Tyro3 polypeptide. In some embodiments, the soluble AXL has a about a 115-fold stronger affinity to GAS6 than the affinity of the wild-type AXL polypeptide.

The ability of a molecule to bind to GAS6 can be determined, for example, by the ability of the putative ligand to bind to GAS6 coated on an assay plate. In one embodiment, the binding activity of AXL, MER or Tyro3 variant polypeptides of the present invention to a GAS6 can be assayed by either immobilizing the ligand, e.g., GAS6 or the AXL, MER or Tyro3 variant polypeptides. For example, the assay can include immobilizing GAS6 fused to a His tag onto Ni-activated NTA resin beads. Agents can be added in an appropriate buffer and the beads incubated for a period of time at a given temperature. After washes to remove unbound material, the bound protein can be released with, for example, SDS, buffers with a high pH, and the like and analyzed.

In still yet other embodiments, AXL, MER or Tyro3 variant polypeptides of the present invention has a better thermal stability than the thermal stability of a wild-type AXL. In some embodiments, the melting temperature of AXL, MER or Tyro3 variant polypeptides of the present invention is at least 5° C., 10° C., 15° C., or 20° C. higher than the melting temperature of a wild-type AXL.

According to the present invention, AXL, MER or Tyro3 variant polypeptides of the present invention can also include one or more modifications that do not alter primary sequences of the AXL, MER or Tyro3 variant polypeptides of the present invention. For example, such modifications can include chemical derivatization of polypeptides, e.g., acetylation, amidation, carboxylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, AXL, MER or Tyro3 polypeptide variants of the present invention include AXL, MER or Tyro3 variant polypeptides having phosphorylated amino acid residues, e.g. phosphotyrosine, phosphoserine, or phosphothreonine.

In some other embodiments, AXL, MER or Tyro3 variant polypeptides of the present invention include AXL, MER or Tyro3 variant polypeptides further modified to improve their resistance to proteolytic degradation or to optimize solubility properties or to render them more suitable as a therapeutic agent. For example, AXL, MER or Tyro3 polypeptide variants of the present invention further include analogs of AXL, MER or Tyro3 variant polypeptides containing residues other than naturally occurring L-amino acids, e.g. D-amino acids or non-naturally occurring synthetic amino acids. D-amino acids may be substituted for some or all of the amino acid residues.

In yet some other embodiments, AXL, MER or Tyro3 variant polypeptides of the present invention include at least two same or different AXL, MER or Tyro3 variant polypeptides linked covalently or non-covalently. For example, in some embodiments, AXL, MER or Tyro3 polypeptide variants of the present invention include two, three, four, five, or six same or different AXL, MER or Tyro3 variant polypeptides linked covalently, e.g., so that they will have the appropriate size, but avoiding unwanted aggregation.

According to the present invention, AXL, MER or Tyro3 variant polypeptides of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The AXL, MER or Tyro3 variant polypeptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The AXL, MER or Tyro3 variant polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

In some embodiments, the present invention provides expression vectors for in vitro or in vivo expression of one or more AXL, MER and/or Tyro3 polypeptide variants of the present invention, either constitutively or under one or more regulatory elements. In some embodiments, the present invention provides a cell population comprising one or more expression vectors for expressing AXL, MER and/or Tyro3 polypeptide variants of the present invention, either constitutively or under one or more regulatory elements.

According to another aspect of the invention, it provides isolated antibodies or fragments thereof which specifically binds to a GAS6 protein. GAS6 (growth arrest-specific 6) belongs structurally to the family of plasma vitamin K-dependent proteins. GAS6 has a high structural homology with the natural anticoagulant protein S, sharing the same modular composition and having 40% sequence identity. GAS6 has growth factor-like properties through its interaction with receptor tyrosine kinases of the TAM family; Tyro3, AXL and MER. Human GAS6 is a 678 amino acid protein that consists of a gamma-carboxyglutamate (Gla)-rich domain that mediates binding to phospholipid membranes, four epidermal growth factor-like domains, and two laminin G-like (LG) domains. The sequence of the transcript variants of human GAS6 may be accessed at Genbank at NM_001143946.1; NM_001143945.1; and NM_000820.2, respectively.

GAS6 employs a unique mechanism of action, interacting through its vitamin K-dependent GLA (gamma-carboxyglutamic acid) module with phosphatidylserine-containing membranes and through its carboxy-terminal LamG domains with the TAM membrane receptors.

According to yet another aspect of the invention, it provides isolated antibodies or fragments thereof which specifically bind to an AXL protein. As described above, the AXL protein, with reference to the native sequence of SEQ ID NO: 1, comprises an immunoglobulin (Ig)-like domain from residues 27-128, a second Ig-like domain from residues 139-222, fibronectin type 3 domains from residues 225-332 and 333-427, intracellular domain from residues 473-894 including tyrosine kinase domain.

According to the present invention, isolated antibodies of the present invention include any isolated antibodies with a recognizable binding specificity against AXL, MER, Tyro3 or GAS6. In some embodiments, isolated antibodies are partially or fully humanized antibodies. In some other embodiments, isolated antibodies are monoclonal or polyclonal antibodies. In yet some other embodiments, isolated antibodies are chimeric antibodies, e.g., with consistent regions, variable regions and/or CDR3 or a combination thereof from different sources. In yet some other embodiments, isolated antibodies are a combination of various features described herein.

According to the present invention, fragments of the isolated antibodies of the present invention include a polypeptide containing a region of the antibody (either in the context of an antibody scaffold or a non-antibody scaffold) that is sufficient or necessary for a recognizable specific binding of the polypeptide towards AXL, MER, Tyro3 or GAS6. In some embodiments, fragments of the isolated antibodies of the present invention include variable light chains, variable heavy chains, one or more CDRs of heavy chains or light chains or combinations thereof, e.g., Fab, Fv, etc. In some embodiments, fragments of the isolated antibodies of the present invention include a polypeptide containing a single chain antibody, e.g., ScFv. In yet some embodiments, fragments of the isolated antibodies of the present invention include variable regions only or variable regions in combination with part of Fc region, e.g., CH1 region. In still some embodiments, fragments of the isolated antibodies of the present invention include minibodies, e.g., VL-VH-CH3 or diabodies.

In another embodiment, the present invention provides isolated antibodies or fragments thereof which specifically bind to a GAS6 protein (SEQ ID NO:11). In some embodiments, the isolated antibody or fragment thereof is a monoclonal antibody, a humanized antibody, a chimeric antibody, a single chain antibody (ScFv), or a combination thereof. In some other embodiments, the isolated antibody or fragment thereof binds an epitope comprised in one or more amino acid regions of GAS6 selected from the group consisting of R299-T317, V364-P372, R389-N396, D398-A406, E413-H429, and W450-M468. In some embodiments, isolated antibodies of the present invention bind to an epitope comprised in or presented by one or more amino acid regions that interact with AXL, MER and/or Tyro3. In yet some other embodiments, isolated antibodies of the present invention bind to an epitope comprised in or presented by one or more amino acid regions of GAS6, e.g., L295-T317, E356-P372, R389-N396, D398-A406, E413-H429, and W450-M468 of GAS6. In yet some other embodiments, isolated antibodies of the present invention bind to an epitope comprised in or presented by one or more amino acid regions, e.g., LRMFSGTPVIRLRFKRLQPT (SEQ ID NO: 4), EIVGRVTSSGP (SEQ ID NO: 5), RNLVIKVN (SEQ ID NO: 6), DAVMKIAVA (SEQ ID NO: 7), ERGLYHLNLTVGIPFH (SEQ ID NO: 8), and WLNGEDTTIQETVVNRM (SEQ ID NO: 9).

In yet some other embodiments, isolated antibodies of the present invention bind to an epitope comprised in or presented by at least one, two, three, four, five, or six amino acids in a region of L295-T317, E356-P372, R389-N396, D398-A406, E413-H429, and W450-M468 of GAS6. In yet some other embodiments, isolated antibodies of the present invention bind to an epitope comprised in or presented by at least one, two, three, four, five or six amino acids in a region of LRMFSGTPVIRLRFKRLQPT (SEQ ID NO: 4), EIVGRVTSSGP (SEQ ID NO: 5), RNLVIKVN (SEQ ID NO: 6), DAVMKIAVA (SEQ ID NO: 7), ERGLYHLNLTVGIPFH (SEQ ID NO: 8), and WLNGEDTTIQETVVNRM (SEQ ID NO: 9).

In still some other embodiments, isolated antibodies of the present invention are capable of inhibiting, inhibit, or compete with the binding between wild-type AXL, MER and/or Tyro3 or AXL, MER and/or Tyro3 polypeptide variants of the present invention and GAS6. Such antibodies can include for example, antibodies that bind to the GAS6/AXL binding domain portions of either AXL and/or GAS6.

According to the present invention, the AXL, MER or Tyro3 variant polypeptides and isolated antibodies of the present invention can be provided in pharmaceutical compositions suitable for therapeutic use, e.g., for human treatment. In some embodiments, pharmaceutical compositions of the present invention include one or more therapeutic entities of the present invention, e.g., AXL polypeptide variants and/or isolated antibodies against GAS6 or pharmaceutically acceptable salts, esters or solvates thereof or any prodrug thereof. In some other embodiments, pharmaceutical compositions of the present invention include one or more therapeutic entities of the present invention in combination with another therapeutic agent, e.g., another agent for treatment of endometriosis, kidney disease, inflammatory disease and/or transplant rejection (GVHD). Such agents can include but are not limited to Leuprolide acetate, Goserelin, Triptorelin pamoate, Dienogest, Danazol, Medroxyprogesterone acetate, Nafarelin and Buserelin. In yet some other embodiments, pharmaceutical compositions of the present invention include one or more therapeutic entities of the present invention in combination with another pharmaceutically acceptable excipient.

In still some other embodiments, therapeutic entities of the present invention are often administered as pharmaceutical compositions comprising an active therapeutic agent, i.e., and a variety of other pharmaceutically acceptable components. (See Remington's Pharmaceutical Science, 15$^{th}$ ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

In yet other embodiments, methods of the present invention include administering to a subject in need of treatment a therapeutically effective amount or an effective dose of a therapeutic entity (e.g., inhibitor agent) of the present invention, e.g., an inhibitor of AXL, MER and/or Tyro3 activity or GAS6 activity or an inhibitor of interaction between AXL, MER and/or Tyro3 and GAS6. In some embodiments, effective doses of the therapeutic entity of the present invention, e.g. for the treatment of endometriosis, kidney disease, inflammatory disease and/or transplant rejection (GVHD), described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

In some embodiments, the dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still yet some other embodiments, for prophylactic applications, pharmaceutical compositions or medicaments are administered to a patient susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In still yet some other embodiments, for therapeutic applications, therapeutic entities of the present invention are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved. Typically, the response is monitored and repeated dosages are given if there is a recurrence of endometriosis, kidney disease, inflammatory disease and/or transplant rejection (GVHD).

According to the present invention, compositions for the treatment of endometriosis, kidney disease, inflammatory disease and/or transplant rejection (GVHD) can be administered by parenteral, topical, intravenous, oral, subcutaneous, intraarterial, intracranial, intraperitoneal, intranasal or intramuscular means. The most typical route of administration is intravenous although other routes can be equally effective.

For parenteral administration, compositions of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies and/or polypeptides can be administered in the form of a depot injection or implant preparation which can be formulated in such a manner as to permit a sustained release of the active ingredient. An exemplary composition comprises polypeptide at 1 mg/mL, formulated in aqueous buffer consisting of 10 mM Tris, 210 mM sucrose, 51 mM L-arginine, 0.01% polysorbate 20, adjusted to pH 7.4 with HCl or NaOH.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., Nature 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., Biochem. Biophys. Acta 1368: 201-15, 1998.

The pharmaceutical compositions are generally formulated as sterile, substantially isotonic and in full compliance with all Good Manufacturing Practice (GMP) regulations of the U.S. Food and Drug Administration.

Preferably, a therapeutically effective dose of the antibody compositions described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1).

Also within the scope of the invention are kits comprising the compositions (e.g., AXL, MER or Tyro3 variant polypeptides and formulations thereof) of the invention and instructions for use. The kit can further contain a least one additional reagent. Kits typically include a label indicating the intended use of the contents of the kit. The term label includes any writing, or recorded material supplied on or with the kit, or which otherwise accompanies the kit.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. It is also understood that the terminology used herein is for the purposes of describing particular embodiments Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the appended claims.

What is claimed is:

1. A method of reducing liver fibrosis in a mammalian patient, the method comprising:
   administering an effective dose of a soluble AXL variant polypeptide wherein said soluble AXL variant polypeptide:
   lacks the AXL transmembrane domain,
   lacks a functional fibronectin (FN) domain,
   has an Ig1 domain, and an Ig2 domain,
   has a set of amino acid substitutions at positions relative to SEQ ID NO:1: G32, A72, D87, V92 and G127; or at positions G32, D87, V92 and G127,
   comprises an Fc domain linked to the AXL variant polypeptide by a linker comprising one or more (GLY)$_4$SER (SEQ ID NO:10) units; and
   wherein said AXL-variant polypeptide exhibits increased affinity of binding to GAS6 compared to wild-type AXL (SEQ ID NO:1).

2. The method of claim 1, wherein said soluble AXL variant polypeptide comprises a set of amino acid substitutions where glycine 32 is replaced with a serine residue, aspartic acid 87 is replaced with a glycine residue, valine 92 is replaced with an alanine residue, and glycine 127 is replaced with an arginine residue, and optionally alanine 72 is replaced with a valine residue.

3. The method of claim 1, wherein said soluble AXL variant polypeptide has an affinity of at least about $1 \times 10^{-8}$ M, $1 \times 10^{-9}$ M, $1 \times 10^{-10}$ M, $1 \times 10^{-11}$ M or $1 \times 10^{-12}$ M for GAS6.

4. The method of claim 1, wherein said soluble AXL variant polypeptide exhibits an affinity to GAS6 that is at least about 5-fold stronger, at least about 10-fold stronger or at least about 20-fold stronger than the affinity of the wild-type AXL polypeptide.

* * * * *

SEQUENCE LISTING

```
<160> NUMBER OF SEQ ID NOS: 11

<210> SEQ ID NO 1
<211> LENGTH: 887
<212> TYPE: PRT
<213> ORGANISM: Homo sapiens

<400> SEQUENCE: 1

Met Gly Arg Val Pro Leu Ala Trp Cys Leu Ala Leu Cys Gly Trp Ala
1               5                   10                  15

Cys Met Ala Pro Arg Gly Thr Gln Ala Glu Glu Ser Pro Phe Val Gly
            20                  25                  30

Asn Pro Gly Asn Ile Thr Gly Ala Arg Gly Leu Thr Gly Thr Leu Arg
        35                  40                  45

Cys Gln Leu Gln Val Gln Gly Glu Pro Pro Glu Val His Trp Leu Arg
    50                  55                  60

Asp Gly Gln Ile Leu Glu Leu Ala Asp Ser Thr Gln Thr Gln Val Pro
65                  70                  75                  80

Leu Gly Glu Asp Glu Gln Asp Asp Trp Ile Val Val Ser Gln Leu Arg
                85                  90                  95

Ile Thr Ser Leu Gln Leu Ser Asp Thr Gly Gln Tyr Gln Cys Leu Val
            100                 105                 110

Phe Leu Gly His Gln Thr Phe Val Ser Gln Pro Gly Tyr Val Gly Leu
        115                 120                 125

Glu Gly Leu Pro Tyr Phe Leu Glu Glu Pro Glu Asp Arg Thr Val Ala
    130                 135                 140

Ala Asn Thr Pro Phe Asn Leu Ser Cys Gln Ala Gln Gly Pro Pro Glu
145                 150                 155                 160

Pro Val Asp Leu Leu Trp Leu Gln Asp Ala Val Pro Leu Ala Thr Ala
                165                 170                 175

Pro Gly His Gly Pro Gln Arg Ser Leu His Val Pro Gly Leu Asn Lys
            180                 185                 190

Thr Ser Ser Phe Ser Cys Glu Ala His Asn Ala Lys Gly Val Thr Thr
        195                 200                 205
```

```
Ser Arg Thr Ala Thr Ile Thr Val Leu Pro Gln Gln Pro Arg Asn Leu
210                 215                 220
His Leu Val Ser Arg Gln Pro Thr Glu Leu Glu Val Ala Trp Thr Pro
225                 230                 235                 240
Gly Leu Ser Gly Ile Tyr Pro Leu Thr His Cys Thr Leu Gln Ala Val
                245                 250                 255
Leu Ser Asn Asp Gly Met Gly Ile Gln Ala Gly Glu Pro Asp Pro Pro
            260                 265                 270
Glu Glu Pro Leu Thr Ser Gln Ala Ser Val Pro Pro His Gln Leu Arg
        275                 280                 285
Leu Gly Ser Leu His Pro His Thr Pro Tyr His Ile Arg Val Ala Cys
290                 295                 300
Thr Ser Ser Gln Gly Pro Ser Ser Trp Thr His Trp Leu Pro Val Glu
305                 310                 315                 320
Thr Pro Glu Gly Val Pro Leu Gly Pro Pro Glu Asn Ile Ser Ala Thr
                325                 330                 335
Arg Asn Gly Ser Gln Ala Phe Val His Trp Gln Glu Pro Arg Ala Pro
            340                 345                 350
Leu Gln Gly Thr Leu Leu Gly Tyr Arg Leu Ala Tyr Gln Gly Gln Asp
        355                 360                 365
Thr Pro Glu Val Leu Met Asp Ile Gly Leu Arg Gln Glu Val Thr Leu
370                 375                 380
Glu Leu Gln Gly Asp Gly Ser Val Ser Asn Leu Thr Val Cys Val Ala
385                 390                 395                 400
Ala Tyr Thr Ala Ala Gly Asp Gly Pro Trp Ser Leu Pro Val Pro Leu
                405                 410                 415
Glu Ala Trp Arg Pro Gly Gln Ala Gln Pro Val His Gln Leu Val Lys
            420                 425                 430
Glu Pro Ser Thr Pro Ala Phe Ser Trp Pro Trp Trp Tyr Val Leu Leu
        435                 440                 445
Gly Ala Val Val Ala Ala Ala Cys Val Leu Ile Leu Ala Leu Phe Leu
450                 455                 460
Val His Arg Arg Lys Lys Glu Thr Arg Tyr Gly Glu Val Phe Glu Pro
465                 470                 475                 480
Thr Val Glu Arg Gly Glu Leu Val Val Arg Tyr Arg Val Arg Lys Ser
                485                 490                 495
Tyr Ser Arg Arg Thr Thr Glu Ala Thr Leu Asn Ser Leu Gly Ile Ser
            500                 505                 510
Glu Glu Leu Lys Glu Lys Leu Arg Asp Val Met Val Asp Arg His Lys
        515                 520                 525
Val Ala Leu Gly Lys Thr Leu Gly Glu Gly Glu Phe Gly Ala Val Met
530                 535                 540
Glu Gly Gln Leu Asn Gln Asp Asp Ser Ile Leu Lys Val Ala Val Lys
545                 550                 555                 560
Thr Met Lys Ile Ala Ile Cys Thr Arg Ser Glu Leu Glu Asp Phe Leu
                565                 570                 575
Ser Glu Ala Val Cys Met Lys Glu Phe Asp His Pro Asn Val Met Arg
            580                 585                 590
Leu Ile Gly Val Cys Phe Gln Gly Ser Glu Arg Glu Ser Phe Pro Ala
        595                 600                 605
Pro Val Val Ile Leu Pro Phe Met Lys His Gly Asp Leu His Ser Phe
610                 615                 620
```

-continued

```
Leu Leu Tyr Ser Arg Leu Gly Asp Gln Pro Val Tyr Leu Pro Thr Gln
625                 630                 635                 640

Met Leu Val Lys Phe Met Ala Asp Ile Ala Ser Gly Met Glu Tyr Leu
            645                 650                 655

Ser Thr Lys Arg Phe Ile His Arg Asp Leu Ala Ala Arg Asn Cys Met
        660                 665                 670

Leu Asn Glu Asn Met Ser Val Cys Val Ala Asp Phe Gly Leu Ser Lys
    675                 680                 685

Lys Ile Tyr Asn Gly Asp Tyr Tyr Arg Gln Gly Arg Ile Ala Lys Met
690                 695                 700

Pro Val Lys Trp Ile Ala Ile Glu Ser Leu Ala Asp Arg Val Tyr Thr
705                 710                 715                 720

Ser Lys Ser Asp Val Trp Ser Phe Gly Val Thr Met Trp Glu Ile Ala
            725                 730                 735

Thr Arg Gly Gln Thr Pro Tyr Pro Gly Val Glu Asn Ser Glu Ile Tyr
        740                 745                 750

Asp Tyr Leu Arg Gln Gly Asn Arg Leu Lys Gln Pro Ala Asp Cys Leu
    755                 760                 765

Asp Gly Leu Tyr Ala Leu Met Ser Arg Cys Trp Glu Leu Asn Pro Gln
770                 775                 780

Asp Arg Pro Ser Phe Thr Glu Leu Arg Glu Asp Leu Glu Asn Thr Leu
785                 790                 795                 800

Lys Ala Leu Pro Pro Ala Gln Glu Pro Asp Glu Ile Leu Tyr Val Asn
            805                 810                 815

Met Asp Glu Gly Gly Gly Tyr Pro Glu Pro Pro Gly Ala Ala Gly Gly
        820                 825                 830

Ala Asp Pro Pro Thr Gln Pro Asp Pro Lys Asp Ser Cys Ser Cys Leu
    835                 840                 845

Thr Ala Ala Glu Val His Pro Ala Gly Arg Tyr Val Leu Cys Pro Ser
850                 855                 860

Thr Thr Pro Ser Pro Ala Gln Pro Ala Asp Arg Gly Ser Pro Ala Ala
865                 870                 875                 880

Pro Gly Gln Glu Asp Gly Ala
            885

<210> SEQ ID NO 2
<211> LENGTH: 999
<212> TYPE: PRT
<213> ORGANISM: Homo sapiens

<400> SEQUENCE: 2

Met Gly Pro Ala Pro Leu Pro Leu Leu Leu Gly Leu Phe Leu Pro Ala
1               5                   10                  15

Leu Trp Arg Arg Ala Ile Thr Glu Ala Arg Glu Glu Ala Lys Pro Tyr
            20                  25                  30

Pro Leu Phe Pro Gly Pro Phe Pro Gly Ser Leu Gln Thr Asp His Thr
        35                  40                  45

Pro Leu Leu Ser Leu Pro His Ala Ser Gly Tyr Gln Pro Ala Leu Met
    50                  55                  60

Phe Ser Pro Thr Gln Pro Gly Arg Pro His Thr Gly Asn Val Ala Ile
65                  70                  75                  80

Pro Gln Val Thr Ser Val Glu Ser Lys Pro Leu Pro Pro Leu Ala Phe
            85                  90                  95

Lys His Thr Val Gly His Ile Ile Leu Ser Glu His Lys Gly Val Lys
        100                 105                 110
```

```
Phe Asn Cys Ser Ile Ser Val Pro Asn Ile Tyr Gln Asp Thr Thr Ile
            115                 120                 125

Ser Trp Trp Lys Asp Gly Lys Glu Leu Leu Gly Ala His His Ala Ile
130                 135                 140

Thr Gln Phe Tyr Pro Asp Asp Glu Val Thr Ala Ile Ile Ala Ser Phe
145                 150                 155                 160

Ser Ile Thr Ser Val Gln Arg Ser Asp Asn Gly Ser Tyr Ile Cys Lys
                165                 170                 175

Met Lys Ile Asn Asn Glu Glu Ile Val Ser Asp Pro Ile Tyr Ile Glu
            180                 185                 190

Val Gln Gly Leu Pro His Phe Thr Lys Gln Pro Glu Ser Met Asn Val
            195                 200                 205

Thr Arg Asn Thr Ala Phe Asn Leu Thr Cys Gln Ala Val Gly Pro Pro
        210                 215                 220

Glu Pro Val Asn Ile Phe Trp Val Gln Asn Ser Ser Arg Val Asn Glu
225                 230                 235                 240

Gln Pro Glu Lys Ser Pro Ser Val Leu Thr Val Pro Gly Leu Thr Glu
                245                 250                 255

Met Ala Val Phe Ser Cys Glu Ala His Asn Asp Lys Gly Leu Thr Val
            260                 265                 270

Ser Lys Gly Val Gln Ile Asn Ile Lys Ala Ile Pro Ser Pro Pro Thr
        275                 280                 285

Glu Val Ser Ile Arg Asn Ser Thr Ala His Ser Ile Leu Ile Ser Trp
290                 295                 300

Val Pro Gly Phe Asp Gly Tyr Ser Pro Phe Arg Asn Cys Ser Ile Gln
305                 310                 315                 320

Val Lys Glu Ala Asp Pro Leu Ser Asn Gly Ser Val Met Ile Phe Asn
                325                 330                 335

Thr Ser Ala Leu Pro His Leu Tyr Gln Ile Lys Gln Leu Gln Ala Leu
            340                 345                 350

Ala Asn Tyr Ser Ile Gly Val Ser Cys Met Asn Glu Ile Gly Trp Ser
        355                 360                 365

Ala Val Ser Pro Trp Ile Leu Ala Ser Thr Thr Glu Gly Ala Pro Ser
        370                 375                 380

Val Ala Pro Leu Asn Val Thr Val Phe Leu Asn Glu Ser Ser Asp Asn
385                 390                 395                 400

Val Asp Ile Arg Trp Met Lys Pro Pro Thr Lys Gln Gln Asp Gly Glu
                405                 410                 415

Leu Val Gly Tyr Arg Ile Ser His Val Trp Gln Ser Ala Gly Ile Ser
            420                 425                 430

Lys Glu Leu Leu Glu Glu Val Gly Gln Asn Gly Ser Arg Ala Arg Ile
        435                 440                 445

Ser Val Gln Val His Asn Ala Thr Cys Thr Val Arg Ile Ala Ala Val
450                 455                 460

Thr Arg Gly Gly Val Gly Pro Phe Ser Asp Pro Val Lys Ile Phe Ile
465                 470                 475                 480

Pro Ala His Gly Trp Val Asp Tyr Ala Pro Ser Ser Thr Pro Ala Pro
                485                 490                 495

Gly Asn Ala Asp Pro Val Leu Ile Ile Phe Gly Cys Phe Cys Gly Phe
            500                 505                 510

Ile Leu Ile Gly Leu Ile Leu Tyr Ile Ser Leu Ala Ile Arg Lys Arg
        515                 520                 525
```

```
Val Gln Glu Thr Lys Phe Gly Asn Ala Phe Thr Glu Glu Asp Ser Glu
    530                 535                 540
Leu Val Val Asn Tyr Ile Ala Lys Lys Ser Phe Cys Arg Arg Ala Ile
545                 550                 555                 560
Glu Leu Thr Leu His Ser Leu Gly Val Ser Glu Glu Leu Gln Asn Lys
                565                 570                 575
Leu Glu Asp Val Val Ile Asp Arg Asn Leu Leu Ile Leu Gly Lys Ile
            580                 585                 590
Leu Gly Glu Gly Glu Phe Gly Ser Val Met Glu Gly Asn Leu Lys Gln
        595                 600                 605
Glu Asp Gly Thr Ser Leu Lys Val Ala Val Lys Thr Met Lys Leu Asp
    610                 615                 620
Asn Ser Ser Gln Arg Glu Ile Glu Glu Phe Leu Ser Glu Ala Ala Cys
625                 630                 635                 640
Met Lys Asp Phe Ser His Pro Asn Val Ile Arg Leu Leu Gly Val Cys
                645                 650                 655
Ile Glu Met Ser Ser Gln Gly Ile Pro Lys Pro Met Val Ile Leu Pro
            660                 665                 670
Phe Met Lys Tyr Gly Asp Leu His Thr Tyr Leu Leu Tyr Ser Arg Leu
        675                 680                 685
Glu Thr Gly Pro Lys His Ile Pro Leu Gln Thr Leu Leu Lys Phe Met
    690                 695                 700
Val Asp Ile Ala Leu Gly Met Glu Tyr Leu Ser Asn Arg Asn Phe Leu
705                 710                 715                 720
His Arg Asp Leu Ala Ala Arg Asn Cys Met Leu Arg Asp Asp Met Thr
                725                 730                 735
Val Cys Val Ala Asp Phe Gly Leu Ser Lys Lys Ile Tyr Ser Gly Asp
            740                 745                 750
Tyr Tyr Arg Gln Gly Arg Ile Ala Lys Met Pro Val Lys Trp Ile Ala
        755                 760                 765
Ile Glu Ser Leu Ala Asp Arg Val Tyr Thr Ser Lys Ser Asp Val Trp
    770                 775                 780
Ala Phe Gly Val Thr Met Trp Glu Ile Ala Thr Arg Gly Met Thr Pro
785                 790                 795                 800
Tyr Pro Gly Val Gln Asn His Glu Met Tyr Asp Tyr Leu Leu His Gly
                805                 810                 815
His Arg Leu Lys Gln Pro Glu Asp Cys Leu Asp Glu Leu Tyr Glu Ile
            820                 825                 830
Met Tyr Ser Cys Trp Arg Thr Asp Pro Leu Asp Arg Pro Thr Phe Ser
        835                 840                 845
Val Leu Arg Leu Gln Leu Glu Lys Leu Leu Glu Ser Leu Pro Asp Val
    850                 855                 860
Arg Asn Gln Ala Asp Val Ile Tyr Val Asn Thr Gln Leu Leu Glu Ser
865                 870                 875                 880
Ser Glu Gly Leu Ala Gln Gly Ser Thr Leu Ala Pro Leu Asp Leu Asn
                885                 890                 895
Ile Asp Pro Asp Ser Ile Ile Ala Ser Cys Thr Pro Arg Ala Ala Ile
            900                 905                 910
Ser Val Val Thr Ala Glu Val His Asp Ser Lys Pro His Glu Gly Arg
        915                 920                 925
Tyr Ile Leu Asn Gly Gly Ser Glu Glu Trp Glu Asp Leu Thr Ser Ala
    930                 935                 940
Pro Ser Ala Ala Val Thr Ala Glu Lys Asn Ser Val Leu Pro Gly Glu
```

```
                945                 950                 955                 960
Arg Leu Val Arg Asn Gly Val Ser Trp Ser His Ser Ser Met Leu Pro
                    965                 970                 975
Leu Gly Ser Ser Leu Pro Asp Glu Leu Leu Phe Ala Asp Asp Ser Ser
                980                 985                 990
Glu Gly Ser Glu Val Leu Met
        995

<210> SEQ ID NO 3
<211> LENGTH: 890
<212> TYPE: PRT
<213> ORGANISM: Homo sapiens

<400> SEQUENCE: 3

Met Ala Leu Arg Arg Ser Met Gly Arg Pro Gly Leu Pro Pro Leu Pro
1               5                   10                  15
Leu Pro Pro Pro Arg Leu Gly Leu Leu Leu Ala Ala Leu Ala Ser
                20                  25                  30
Leu Leu Leu Pro Glu Ser Ala Ala Ala Gly Leu Lys Leu Met Gly Ala
            35                  40                  45
Pro Val Lys Leu Thr Val Ser Gln Gly Gln Pro Val Lys Leu Asn Cys
    50                  55                  60
Ser Val Glu Gly Met Glu Pro Asp Ile Gln Trp Val Lys Asp Gly
65                  70                  75                  80
Ala Val Val Gln Asn Leu Asp Gln Leu Tyr Ile Pro Val Ser Glu Gln
                85                  90                  95
His Trp Ile Gly Phe Leu Ser Leu Lys Ser Val Glu Arg Ser Asp Ala
                100                 105                 110
Gly Arg Tyr Trp Cys Gln Val Glu Asp Gly Gly Glu Thr Glu Ile Ser
            115                 120                 125
Gln Pro Val Trp Leu Thr Val Glu Gly Val Pro Phe Phe Thr Val Glu
    130                 135                 140
Pro Lys Asp Leu Ala Val Pro Pro Asn Ala Pro Phe Gln Leu Ser Cys
145                 150                 155                 160
Glu Ala Val Gly Pro Pro Glu Pro Val Thr Ile Val Trp Trp Arg Gly
                165                 170                 175
Thr Thr Lys Ile Gly Gly Pro Ala Pro Ser Pro Ser Val Leu Asn Val
                180                 185                 190
Thr Gly Val Thr Gln Ser Thr Met Phe Ser Cys Glu Ala His Asn Leu
            195                 200                 205
Lys Gly Leu Ala Ser Ser Arg Thr Ala Thr Val His Leu Gln Ala Leu
    210                 215                 220
Pro Ala Ala Pro Phe Asn Ile Thr Val Thr Lys Leu Ser Ser Ser Asn
225                 230                 235                 240
Ala Ser Val Ala Trp Met Pro Gly Ala Asp Gly Arg Ala Leu Leu Gln
                245                 250                 255
Ser Cys Thr Val Gln Val Thr Gln Ala Pro Gly Gly Trp Glu Val Leu
                260                 265                 270
Ala Val Val Val Pro Val Pro Pro Phe Thr Cys Leu Leu Arg Asp Leu
            275                 280                 285
Val Pro Ala Thr Asn Tyr Ser Leu Arg Val Arg Cys Ala Asn Ala Leu
    290                 295                 300
Gly Pro Ser Pro Tyr Ala Asp Trp Val Pro Phe Gln Thr Lys Gly Leu
305                 310                 315                 320
```

```
Ala Pro Ala Ser Ala Pro Gln Asn Leu His Ala Ile Arg Thr Asp Ser
                325                 330                 335

Gly Leu Ile Leu Glu Trp Glu Val Ile Pro Glu Ala Pro Leu Glu
        340                 345                 350

Gly Pro Leu Gly Pro Tyr Lys Leu Ser Trp Val Gln Asp Asn Gly Thr
            355                 360                 365

Gln Asp Glu Leu Thr Val Glu Gly Thr Arg Ala Asn Leu Thr Gly Trp
370                 375                 380

Asp Pro Gln Lys Asp Leu Ile Val Arg Val Cys Val Ser Asn Ala Val
385                 390                 395                 400

Gly Cys Gly Pro Trp Ser Gln Pro Leu Val Val Ser Ser His Asp Arg
                405                 410                 415

Ala Gly Gln Gln Gly Pro Pro His Ser Arg Thr Ser Trp Val Pro Val
            420                 425                 430

Val Leu Gly Val Leu Thr Ala Leu Val Thr Ala Ala Leu Ala Leu
                435                 440                 445

Ile Leu Leu Arg Lys Arg Lys Glu Thr Arg Phe Gly Gln Ala Phe
        450                 455                 460

Asp Ser Val Met Ala Arg Gly Glu Pro Ala Val His Phe Arg Ala Ala
465                 470                 475                 480

Arg Ser Phe Asn Arg Glu Arg Pro Glu Arg Ile Glu Ala Thr Leu Asp
                485                 490                 495

Ser Leu Gly Ile Ser Asp Glu Leu Lys Glu Lys Leu Glu Asp Val Leu
            500                 505                 510

Ile Pro Glu Gln Gln Phe Thr Leu Gly Arg Met Leu Gly Lys Gly Glu
        515                 520                 525

Phe Gly Ser Val Arg Glu Ala Gln Leu Lys Gln Glu Asp Gly Ser Phe
530                 535                 540

Val Lys Val Ala Val Lys Met Leu Lys Ala Asp Ile Ile Ala Ser Ser
545                 550                 555                 560

Asp Ile Glu Glu Phe Leu Arg Glu Ala Ala Cys Met Lys Glu Phe Asp
                565                 570                 575

His Pro His Val Ala Lys Leu Val Gly Val Ser Leu Arg Ser Arg Ala
            580                 585                 590

Lys Gly Arg Leu Pro Ile Pro Met Val Ile Leu Pro Phe Met Lys His
        595                 600                 605

Gly Asp Leu His Ala Phe Leu Leu Ala Ser Arg Ile Gly Glu Asn Pro
610                 615                 620

Phe Asn Leu Pro Leu Gln Thr Leu Ile Arg Phe Met Val Asp Ile Ala
625                 630                 635                 640

Cys Gly Met Glu Tyr Leu Ser Ser Arg Asn Phe Ile His Arg Asp Leu
                645                 650                 655

Ala Ala Arg Asn Cys Met Leu Ala Glu Asp Met Thr Val Cys Val Ala
            660                 665                 670

Asp Phe Gly Leu Ser Arg Lys Ile Tyr Ser Gly Asp Tyr Tyr Arg Gln
        675                 680                 685

Gly Cys Ala Ser Lys Leu Pro Val Lys Trp Leu Ala Leu Glu Ser Leu
690                 695                 700

Ala Asp Asn Leu Tyr Thr Val Gln Ser Asp Val Trp Ala Phe Gly Val
705                 710                 715                 720

Thr Met Trp Glu Ile Met Thr Arg Gly Gln Thr Pro Tyr Ala Gly Ile
                725                 730                 735

Glu Asn Ala Glu Ile Tyr Asn Tyr Leu Ile Gly Gly Asn Arg Leu Lys
```

-continued

```
                  740                 745                 750
Gln Pro Pro Glu Cys Met Glu Asp Val Tyr Asp Leu Met Tyr Gln Cys
            755                 760                 765

Trp Ser Ala Asp Pro Lys Gln Arg Pro Ser Phe Thr Cys Leu Arg Met
770                 775                 780

Glu Leu Glu Asn Ile Leu Gly Gln Leu Ser Val Leu Ser Ala Ser Gln
785                 790                 795                 800

Asp Pro Leu Tyr Ile Asn Ile Glu Arg Ala Glu Glu Pro Thr Ala Gly
                805                 810                 815

Gly Ser Leu Glu Leu Pro Gly Arg Asp Gln Pro Tyr Ser Gly Ala Gly
            820                 825                 830

Asp Gly Ser Gly Met Gly Ala Val Gly Gly Thr Pro Ser Asp Cys Arg
835                 840                 845

Tyr Ile Leu Thr Pro Gly Gly Leu Ala Glu Gln Pro Gly Gln Ala Glu
            850                 855                 860

His Gln Pro Glu Ser Pro Leu Asn Glu Thr Gln Arg Leu Leu Leu Leu
865                 870                 875                 880

Gln Gln Gly Leu Leu Pro His Ser Ser Cys
                885                 890

<210> SEQ ID NO 4
<211> LENGTH: 20
<212> TYPE: PRT
<213> ORGANISM: Homo sapiens

<400> SEQUENCE: 4

Leu Arg Met Phe Ser Gly Thr Pro Val Ile Arg Leu Arg Phe Lys Arg
1               5                   10                  15

Leu Gln Pro Thr
            20

<210> SEQ ID NO 5
<211> LENGTH: 11
<212> TYPE: PRT
<213> ORGANISM: Homo sapiens

<400> SEQUENCE: 5

Glu Leu Val Gly Arg Val Thr Ser Ser Gly Pro
1               5                   10

<210> SEQ ID NO 6
<211> LENGTH: 8
<212> TYPE: PRT
<213> ORGANISM: Homo sapiens

<400> SEQUENCE: 6

Arg Asn Leu Val Ile Lys Val Asn
1               5

<210> SEQ ID NO 7
<211> LENGTH: 9
<212> TYPE: PRT
<213> ORGANISM: Homo sapiens

<400> SEQUENCE: 7

Asp Ala Val Met Lys Ile Ala Val Ala
1               5

<210> SEQ ID NO 8
<211> LENGTH: 16
```

```
<212> TYPE: PRT
<213> ORGANISM: Homo sapiens

<400> SEQUENCE: 8

Glu Arg Gly Leu Tyr His Leu Asn Leu Thr Val Gly Ile Pro Phe His
1               5                   10                  15

<210> SEQ ID NO 9
<211> LENGTH: 17
<212> TYPE: PRT
<213> ORGANISM: Homo sapiens

<400> SEQUENCE: 9

Trp Leu Asn Gly Glu Asp Thr Thr Ile Gln Glu Thr Val Val Asn Arg
1               5                   10                  15

Met

<210> SEQ ID NO 10
<211> LENGTH: 5
<212> TYPE: PRT
<213> ORGANISM: Artificial Sequence
<220> FEATURE:
<223> OTHER INFORMATION: Synthetic Linker

<400> SEQUENCE: 10

Gly Gly Gly Gly Ser
1               5

<210> SEQ ID NO 11
<211> LENGTH: 19
<212> TYPE: PRT
<213> ORGANISM: Homo sapiens

<400> SEQUENCE: 11

Arg Met Phe Ser Gly Thr Pro Val Ile Arg Leu Arg Phe Lys Arg Leu
1               5                   10                  15

Gln Pro Thr
```